US011786627B2

(12) United States Patent
Lyu et al.

(10) Patent No.: US 11,786,627 B2
(45) Date of Patent: Oct. 17, 2023

(54) RESPIRATORY DROPLET-ABSORBING DEVICE AND AN APPARATUS AND SYSTEM INCLUDING THE SAME

(71) Applicant: Guangzhou Ajax Medical Equipment Co., Ltd., Guangzhou (CN)

(72) Inventors: Bing Lyu, Guangzhou (CN); Yuansheng Zhou, Guangzhou (CN); Xuehua Huang, Guangzhou (CN); Qing Xiang, Guangzhou (CN); Zhijie Li, Guangzhou (CN)

(73) Assignee: Guangzhou Ajax Medical Equipment Co., Ltd., Guangzhou (CN)

( * ) Notice: Subject to any disclaimer, the term of this patent is extended or adjusted under 35 U.S.C. 154(b) by 676 days.

(21) Appl. No.: 16/862,536

(22) Filed: Apr. 29, 2020

(65) Prior Publication Data

US 2021/0275715 A1 Sep. 9, 2021

(30) Foreign Application Priority Data

Mar. 6, 2020 (CN) .......................... 202020266645.0
Apr. 10, 2020 (CN) .......................... 202020522009.X
Apr. 17, 2020 (CN) .......................... 202020572256.0
Apr. 23, 2020 (CN) .......................... 202020628200.2
Apr. 23, 2020 (CN) .......................... 202020628256.8

(51) Int. Cl.
*A61L 9/20* (2006.01)
*B01D 46/00* (2022.01)
(Continued)

(52) U.S. Cl.
CPC .......... *A61L 9/205* (2013.01); *B01D 46/0005* (2013.01); *B01D 46/0028* (2013.01);
(Continued)

(58) Field of Classification Search
CPC .. A61L 9/205; A61L 2209/12; A61L 2209/14; B01D 46/0028; B01D 46/0036;
(Continued)

(56) References Cited

U.S. PATENT DOCUMENTS

2005/0008549 A1* 1/2005 Hsu .................... A61L 9/205
422/186
2007/0251812 A1* 11/2007 Hayman .............. B01D 53/007
422/186.3
(Continued)

FOREIGN PATENT DOCUMENTS

CN 205878393 U * 1/2017
JP 2005342509 A * 12/2005
(Continued)

OTHER PUBLICATIONS

European Search Opinion for Application No. 20 198 599.1 (Year: 2021).*

*Primary Examiner* — Jennifer Wecker
*Assistant Examiner* — Brady C Pilsbury
(74) *Attorney, Agent, or Firm* — Bayramoglu Law Offices LLC

(57) ABSTRACT

A respiratory droplet suction device includes an air inlet end and an exhaust end. A plurality of filtering devices are arranged between the air inlet end and the exhaust end. The filtering device is provided with a bacteria filtering screen for adsorbing bacteria and an ultraviolet sterilization lamp for inactivating the bacteria. The filtering device includes a first side wall and a second side wall. The first side wall is connected to the air inlet end, and the second side wall is connected to the exhaust end. The air entering from the first side wall is filtered by the bacteria filtering screen and discharged through the second side wall. The ultraviolet sterilization lamp is arranged corresponding to the bacteria filtering screen. A respiratory droplet filtering apparatus includes the respiratory droplet suction device, and a respiratory droplet electric suction system includes the respiratory droplet filtering apparatus are further provided.

32 Claims, 40 Drawing Sheets

(51) Int. Cl.
  *B01D 46/52* (2006.01)
  *B01D 46/58* (2022.01)
  *B01D 46/62* (2022.01)
  *F24F 8/108* (2021.01)
  *F24F 8/22* (2021.01)

(52) U.S. Cl.
  CPC ..... *B01D 46/0036* (2013.01); *B01D 46/0038* (2013.01); *B01D 46/0043* (2013.01); *B01D 46/521* (2013.01); *B01D 46/58* (2022.01); *B01D 46/62* (2022.01); *F24F 8/108* (2021.01); *F24F 8/22* (2021.01); *A61L 2209/12* (2013.01); *A61L 2209/14* (2013.01); *A61L 2209/15* (2013.01); *B01D 2267/40* (2013.01); *B01D 2275/20* (2013.01); *B01D 2279/65* (2013.01)

(58) Field of Classification Search
  CPC .... B01D 46/58; B01D 46/62; B01D 2279/65; F24F 8/22; F24F 8/167
  See application file for complete search history.

(56) References Cited

U.S. PATENT DOCUMENTS

| | | | |
|---|---|---|---|
| 2009/0041632 A1* | 2/2009 | Day | A61L 9/205 422/121 |
| 2009/0320678 A1* | 12/2009 | Chang | B01D 46/62 95/134 |
| 2010/0209312 A1* | 8/2010 | Pastor | A61L 9/205 422/186 |
| 2012/0285459 A1* | 11/2012 | Sata | F24F 8/80 128/205.27 |
| 2013/0189162 A1* | 7/2013 | Jeong | A61L 9/205 422/121 |
| 2020/0061231 A1* | 2/2020 | Jeong | B01D 46/0004 |
| 2021/0170062 A1* | 6/2021 | Hu | A61L 9/205 |

FOREIGN PATENT DOCUMENTS

| | | | | |
|---|---|---|---|---|
| KR | 20110001637 A | * | 1/2011 | |
| KR | 20150112161 A | * | 10/2015 | |
| WO | WO-2019046648 A1 | * | 3/2019 | ............. A61L 2/022 |

* cited by examiner

RESPIRATORY DROPLET-ABSORBING DEVICE AND AN APPARATUS AND SYSTEM INCLUDING THE SAME

CROSS REFERENCE TO THE RELATED APPLICATIONS

This application is based upon and claims the following five priorities to Chinese Patent Applications: No. 202020266645.0 filed on Mar. 6, 2020; No. 202020572256.0 filed on Apr. 17, 2020; No. 202020522009.X filed on Apr. 10, 2020; No. 202020628200.2 filed on Apr. 23, 2020; and No. 202020628256.8 filed on Apr. 23, 2020, and the entire contents of which are incorporated herein by reference.

TECHNICAL FIELD

The present invention relates to a medical respiratory device, and more particularly, to a medical device for collecting human respiratory droplets and inactivating the bacteria present therein during a medical process.

BACKGROUND

In the process of medical treatment, typically in the treatment of oral diseases, medical staff and patients share and exchange respiratory gases for extended periods. Shared breathing times often last hours. Since infectious gases and respiratory droplets are easily produced, cross-infection between the medical staff and the oral disease patient is likely to occur. This can happen if the patient has an infectious disease or, conversely, if the medical staff has infectious disease. It is imperative, therefore, to develop medical security equipment capable of blocking such cross-infection. The new equipment should be capable of ensuring there is no possible chance of infection between the medical staff and the patient during medical treatment.

In view of the above-mentioned issues, it is highly desirable to develop a respiratory droplet suction device capable of collecting and inactivating bacteria and an apparatus and system including the device.

SUMMARY

An object of the present invention is to provide a medical device for the treatment of oral diseases, which can filter and inactivate bacteria.

The present invention provides a respiratory droplet suction device, including an air inlet end and an exhaust end. A filtering unit is arranged between the air inlet end and the exhaust end. The filtering unit is provided with a bacteria filtering screen for filtering and adsorbing bacteria and an ultraviolet sterilization lamp for inactivating the bacteria.

The filtering unit includes a first side wall and a second side wall. The first side wall is connected to the air inlet end, and the second side wall is connected to the exhaust end. The air entering the air inlet end is filtered by the bacteria filtering screen and discharged from the exhaust end.

The ultraviolet sterilization lamp is arranged between the first side wall and the bacteria filtering screen. The ultraviolet sterilization lamp is arranged corresponding to the bacteria filtering screen. Further, the bacteria filtering screen includes a windward surface, and an irradiation cavity is arranged between the first side wall and the bacteria filtering screen. The light of the ultraviolet sterilization lamp is scattered on the windward surface through the irradiation cavity.

Further, a photocatalyst is arranged in the irradiation cavity, and the photocatalyst is arranged above the bacteria filtering screen.

Further, a photocatalyst is arranged in the irradiation cavity, and the photocatalyst is arranged on the periphery of the ultraviolet sterilization lamp.

Further, the filtering unit is provided with a plurality of ultraviolet sterilization lamps.

Further, the suction device includes a plurality of filtering devices connected in parallel.

Further, the suction device includes a plurality of filtering devices connected in series.

With respect to the respiratory droplet suction device, the present invention further provides a respiratory droplet filtering apparatus, which is convenient to assemble and disassemble and has a good sealing effect.

The respiratory droplet filtering apparatus includes an air intake pipe, an exhaust pipe, a fan for providing power, and a treatment unit for filtering and sterilizing the intake air. The treatment unit includes a front filtering mechanism and a bacteria filtering mechanism. The bacteria filtering mechanism includes the suction device. The fan is arranged between the front filtering mechanism and the bacteria filtering mechanism, and the air intake pipe is connected to the front filtering mechanism. The exhaust pipe is connected to the bacteria filtering mechanism, and the bacteria filtering mechanism is connected to the front filtering mechanism. The air intake pipe is connected to the air inlet end of the suction device, and the exhaust pipe is connected to the exhaust end of the suction device.

Further, the front filtering mechanism includes a front filtering screen, a front buckle plate and a front receiving cavity. The front filtering screen includes a main panel and a secondary panel. There is a smooth transition between the main panel and the secondary panel. The front buckle plate, the secondary panel and the front receiving cavity are laminated together.

Further, the bacteria filtering mechanism includes a rear buckle plate and a rear receiving cavity. The bacteria filtering screen includes an upper connecting surface and a lower connecting surface. The rear buckle plate, the lower connecting surface, the upper connecting surface and the rear receiving cavity are laminated together.

Further, the filtering device includes a spring lock for locking and pressing the front filtering mechanism and/or the bacteria filtering mechanism. The spring lock includes a retractable elastic arm arranged between the front buckle plate and the front receiving cavity.

Further, the spring lock includes a lock body and a buckle body. The lock body includes a retractable portion and an anti-release portion. The retractable portion includes a fixed base, a flipping member and a hanging buckle. The buckle body is fixed on the front buckle plate and/or the rear buckle plate, and the fixed base is fixed on the front receiving cavity and/or the rear receiving cavity. The upper end of the flipping member is connected to the fixed base, and the middle portion of the flipping member is pivotally connected to the hanging buckle.

Further, the retractable arm includes a retractable spring, an upper hanging member, a lower hanging member, a front connecting shaft and a rear connecting shaft. The retractable spring includes a retractable body and a spring cavity formed in the retractable body. One end of the upper hanging member is an upper anti-release end, and the other end of the upper hanging member passes through the spring cavity from the upper end of the retractable spring and is connected to the front connecting shaft. One end of the lower hanging member is a lower anti-release end, and the other end of the lower hanging member passes through the spring cavity from the lower end of the retractable spring and is connected to the rear connecting shaft.

Further, the anti-release portion includes a pin, a pin reset spring, and a barb arranged on the fixed base. The pin includes a pin reset base, a pin notch and a limiting tooth. The flipping member is provided with a pin hole and a socket allowing one end of the pin to pass through the pin hole, and the socket is configured to fix the pin reset base. The pin passes through the pin hole and the pin reset spring, and is inserted in the socket.

Further, the flipping member has a U-shaped cross section and includes two opposing side walls. The pin hole and the socket are oppositely disposed, respectively, on the two side walls. The barb is arranged in the pin notch. The spring lock structure is designed to enhance the airtightness of the filtering screen and the device body. After being filtered by the bacteria filtering mechanism, the bacteria are inactivated in time by the ultraviolet sterilization lamp, thereby preventing a bacterial infection caused by the backflow of the bacteria.

Further, the bacteria filtering screen includes the windward surface, a frame and a filtering screen.

The frame covers the outer edge of the filtering screen along the longitudinal direction. One side of the frame on which the windward surface is arranged is provided with a receiving portion, a plurality of partition profiles and a plurality of connectors for ensuring tight connection. The plurality of connectors are configured end-to-end and connected, respectively, to the plurality of partition profiles successively at intervals, and there is a smooth transition between a surface of the connector and a surface of the partition profile.

The filtering screen has a polygonal shape, and the plurality of partition profiles are all connected to the plurality of connectors.

Further, a length-width-height ratio of the filtering device is 15-25:15-25:3-9.

Further, a length, a width and a height of the filtering device are 190-200 mm, 190-200 mm and 45-55 mm, respectively.

Further, the bacteria filtering screen further includes a rigid fixed support, and the fixed support is arranged on one side of the windward surface and is connected to the partition profile.

Further, a surface of the fixed support is provided with a photocatalyst coating.

Further, the fixed support is arranged on both sides of the filtering screen.

Further, the receiving portion extends toward the filtering screen to form a C-shaped cross section of the partition profile.

Further, a receiving cotton is arranged above the receiving portion.

Further, the filtering screen includes a plurality of filtering blades arranged in an alternating crest-and-trough fashion, a wavy shape, and the filtering blades are made of glass fibers. A redundant dust cavity is formed between any two filtering blades opposite to each other.

Further, the filtering screen further includes a shaping frame. The shaping frame is arranged in a corresponding manner to each of the filtering blades. The inner surface of the V-shaped opening is adsorbed on the filtering blades.

Further, the front filtering screen has a concave shape, or in the shape of a cavity. One end of the front filtering screen is provided with a front filtering screen air inlet, and the other end of the front filtering screen is closed. An air intake panel includes a panel air intake hole, the main panel and the secondary panel. The panel air intake hole is arranged in the middle of the main panel, and the secondary panel is arranged on the periphery of the main panel. The secondary panel extends outward along the periphery of the main panel and is in a plane shape. The panel air intake hole, the front filtering screen air inlet and the front filtering screen are arranged in sequence.

Further, the secondary panel is annular and has an outer diameter of less than 190 mm and an inner diameter of more than 120 mm. The panel air intake hole has a diameter ranging from 35 mm to 100 mm. The front filtering screen has a height ranging from 45 mm to 120 mm.

Further, the front filtering screen includes an inner ring surface and an outer ring surface. A panel outer flanging is arranged between the main panel and the secondary panel, and the panel outer flanging is arranged along the outer ring surface.

A panel inner flanging is arranged at the panel air intake hole toward the front filtering screen air inlet, and the panel inner flanging is arranged along the inner ring surface. The inner ring surface is smooth, which facilitates the assembly of the product and can be used in conjunction with the external mechanism. The frame is formed by connecting the partition profiles and the connectors together, and thus has a simple structure and is convenient to assemble, which can effectively improve the production rate, and the partition profiles are readily available. A drop distance is formed on the side of the windward surface to effectively enlarge the space for inactivating the bacteria. The fixed support not only prevents the filtering screen against deformation or damage, but also has the function of applying the coating to increase the photocatalyst effect.

Further, the front filtering screen device further includes a lower end panel, and the lower end panel is provided with a lower end outer flanging and a lower end inner flanging. The lower end outer flanging is arranged at the lower part of the front filtering screen along the outer ring surface of the front filtering screen, and the lower end inner flanging is arranged at the lower part of the front filtering screen along the inner ring surface of the front filtering screen.

Further, the inner side of the inner ring surface is provided with a muffling wall, and the muffling wall is provided with a plurality of arrayed muffling through holes, wherein the air flows through the arrayed muffling through holes into the inner ring surface.

Based on the filtering apparatus of the present invention, the present invention further provides a respiratory droplet electric suction system, which has the functions of being retractable, muffling and filtering. The respiratory droplet electric suction system includes a suction arm and a main body.

The main body includes a housing, an air intake port, a fan, a filtering mechanism, a muffling mechanism and an exhaust mechanism.

The suction arm includes a first end and a second end, the second end is connected to the air intake port, and the first end is provided with an opening for air admission. In operation, the air is pumped by the fan to successively pass through the opening, the first end, the second end and the air intake port into the main body.

The fan, the filtering mechanism and the muffling mechanism are all arranged in the housing. The air flows through the filtering mechanism and the fan, and is then discharged through the exhaust mechanism. The exhaust mechanism includes an exhaust port, and the exhaust port is arranged at the top of the housing and configured to discharge the air out of the top of the housing.

Further, an air guide sleeve is arranged above the exhaust port, and the air guide sleeve extends upward from the top of the housing.

Further, the air guide sleeve guides the air to flow from the top of the housing to a side wall of the housing to discharge the air downward, and a filter cotton is arranged in the air guide sleeve.

Further, the suction arm includes a fixed arm arranged vertically and fixed on the upper portion of the housing, a long arm pivotally connected to the other end of the fixed arm, a short arm pivotally connected to the other end of the long arm, and a positioning arm pivotally connected to the short arm. An opening is arranged at the front end of the positioning arm, and the opening has an incrementally decreasing size toward one end of the positioning arm. A filter cotton is arranged in the short arm.

Further, a sound insulation cotton with a concave portion and a convex portion is arranged on an outer wall of an inner liner and an inner wall of a shell.

The present invention has the following advantages. During the treatment of oral diseases for patients, the respiratory droplets from the oral cavity and the respiratory gases can be collected and filtered, and the bacteria therein can be inactivated, so as to avoid the cross infection between the patient and the medical staff through bacterial colonies.

According to the respiratory droplet suction device provided by the present invention, the ultraviolet sterilization lamp is arranged at the front side of the bacteria filtering screen to inactivate the bacteria deposited on the bacteria filtering screen.

The upper end of the muffling wall is fixedly connected to the panel inner flanging, and the lower end of the muffling wall is connected to the lower end inner flanging. The filtering device with an appropriate size is arranged to match the corresponding model of the apparatus, and thus the front filtering screen provided by the present invention is made universally compatible with all units. The air intake panel and the lower end panel are arranged on the two end surfaces of the front filtering screen, respectively. The lower end panel seals the lower end of the front filtering screen to form a closed cavity. The air entering from the air intake panel flows unidirectionally, and is filtered by the filtering screen on the inner ring surface of the front filtering screen, so that the dust particles in the air are filtered. The main panel and the secondary panel are arranged to connect the front filtering screen and the ring surface corresponding to the front filtering screen, so that the air entering the filtering device can be discharged only after being filtered by the front filtering screen, thus ensuring the quality of the discharged air. The air intake panel is provided with the flanging corresponding to the inner ring surface, and the lower end panel is provided with the flanging corresponding to the outer ring surface. The flanging structure can form a groove carrying a certain amount of fluid. By adding the adhesive to the groove, the front filtering screen can be securely bonded to the groove, which adds to the quality and life of the apparatus.

The spring lock structure is designed to enhance the airtightness of the filtering screen and the device body. After being filtered through the bacteria filtering mechanism, the bacteria are inactivated by the ultraviolet sterilization lamp in time to prevent a bacterial infection caused by the backflow of the bacteria. The retractable arm is configured to ensure the device is hermetically sealed.

The fan is configured to provide kinetic energy to cause the air flow in the respiratory droplet electric suction device to flow in an orderly direction so that the suction is generated at the opening to quickly pump the nearby air flow into the housing. The opening 11 is placed around the mouth of the oral disease patient to suck the air flow, so that the air flow between the doctor and the patient can be effectively pumped into the interior of the suction device for filtration and sterilization. Specifically, the particles, powder and water mist produced during the oral surgery can be collected, and then filtered and sterilized many times, so as to avoid the cross-infection caused by the bacteria and viruses and ensure safety, sterility, and no infection during the oral surgery.

The filter cotton is arranged in the short arm to perform the first filtration, and the front filtering screen and the bacteria filtering screen perform the second filtration and the third filtration, respectively. After being filtered for the fourth time, the bacteria and viruses are inactivated by the ultraviolet sterilization lamp.

The filter cotton of the present invention also has the sound-absorbing function, and the filter cottons arranged in the short arm and the air guide sleeve are significantly effective for sound insulation. The muffling mechanism adjusts the air flow as a whole to increase the muffling distance. The air guide mechanism is configured to control the discharge direction of the air. This makes the product of the present invention especially adaptable to fit the environments for most all applications.

DETAILED DESCRIPTION OF THE EMBODIMENTS

Figure 1:
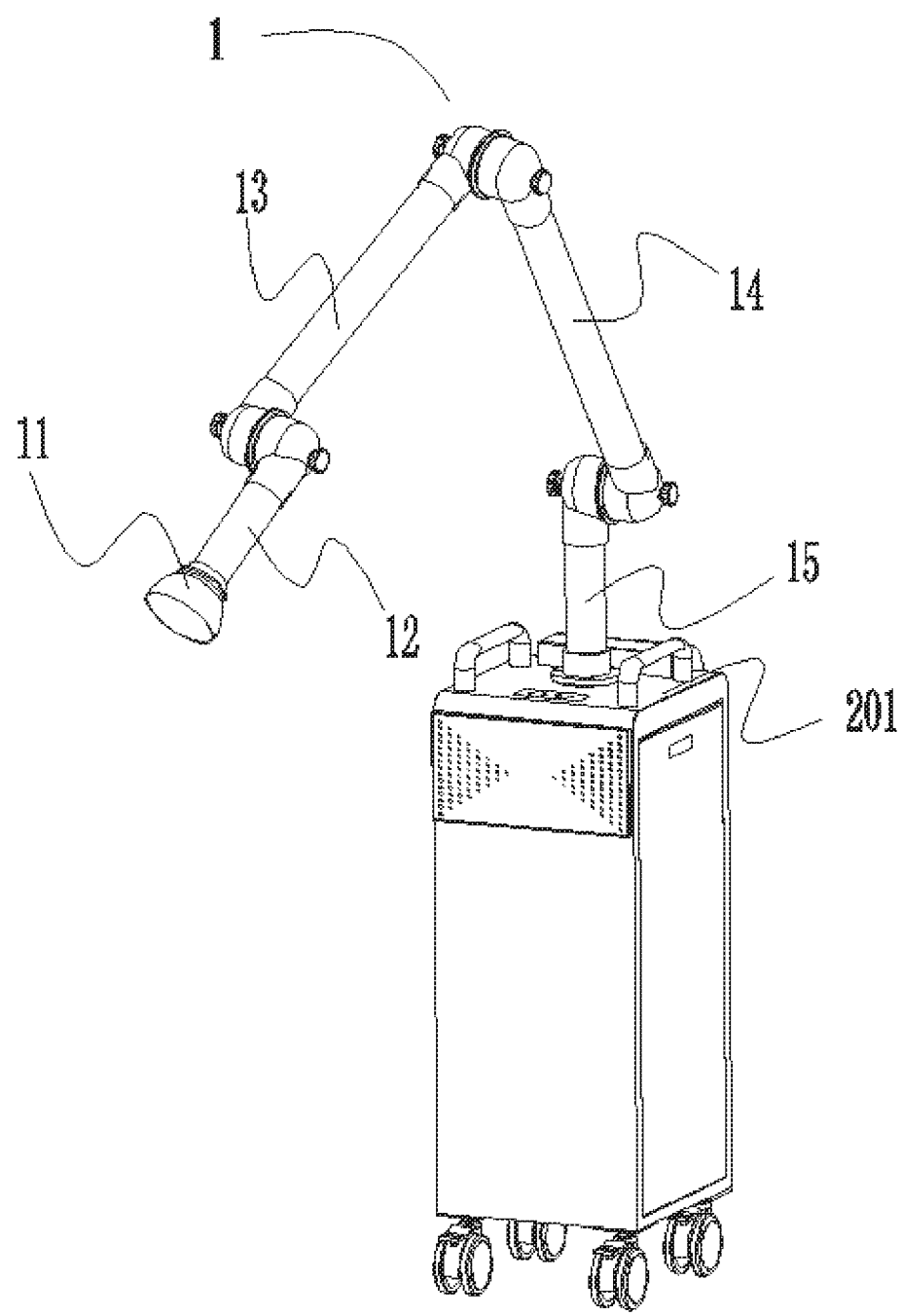
FIG. 1 is a perspective view showing the structures of the whole suction device of the present invention.
Figure 2:
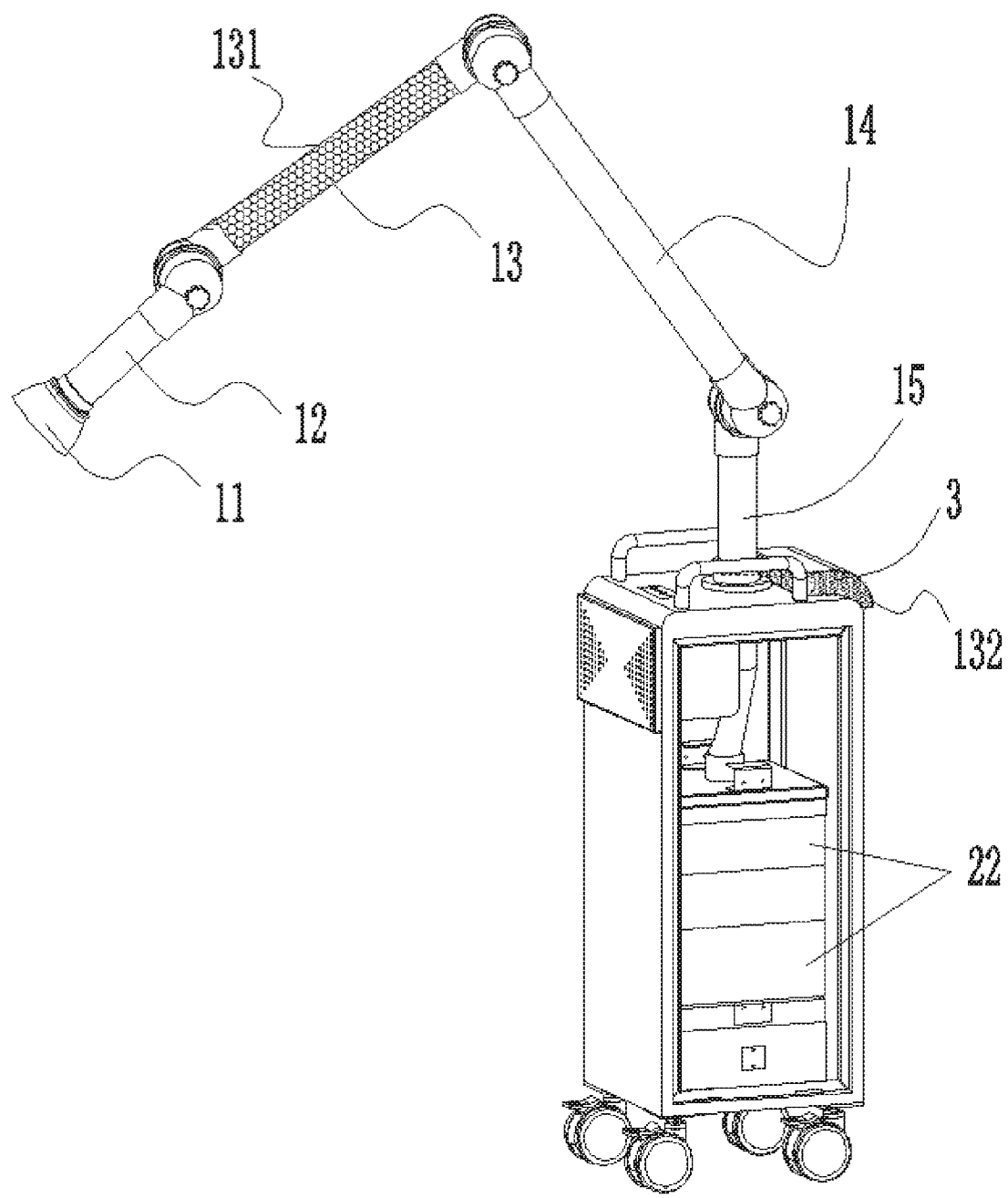
FIG. 2 is a cross-sectional view of a structure of the present invention.
Figure 3:
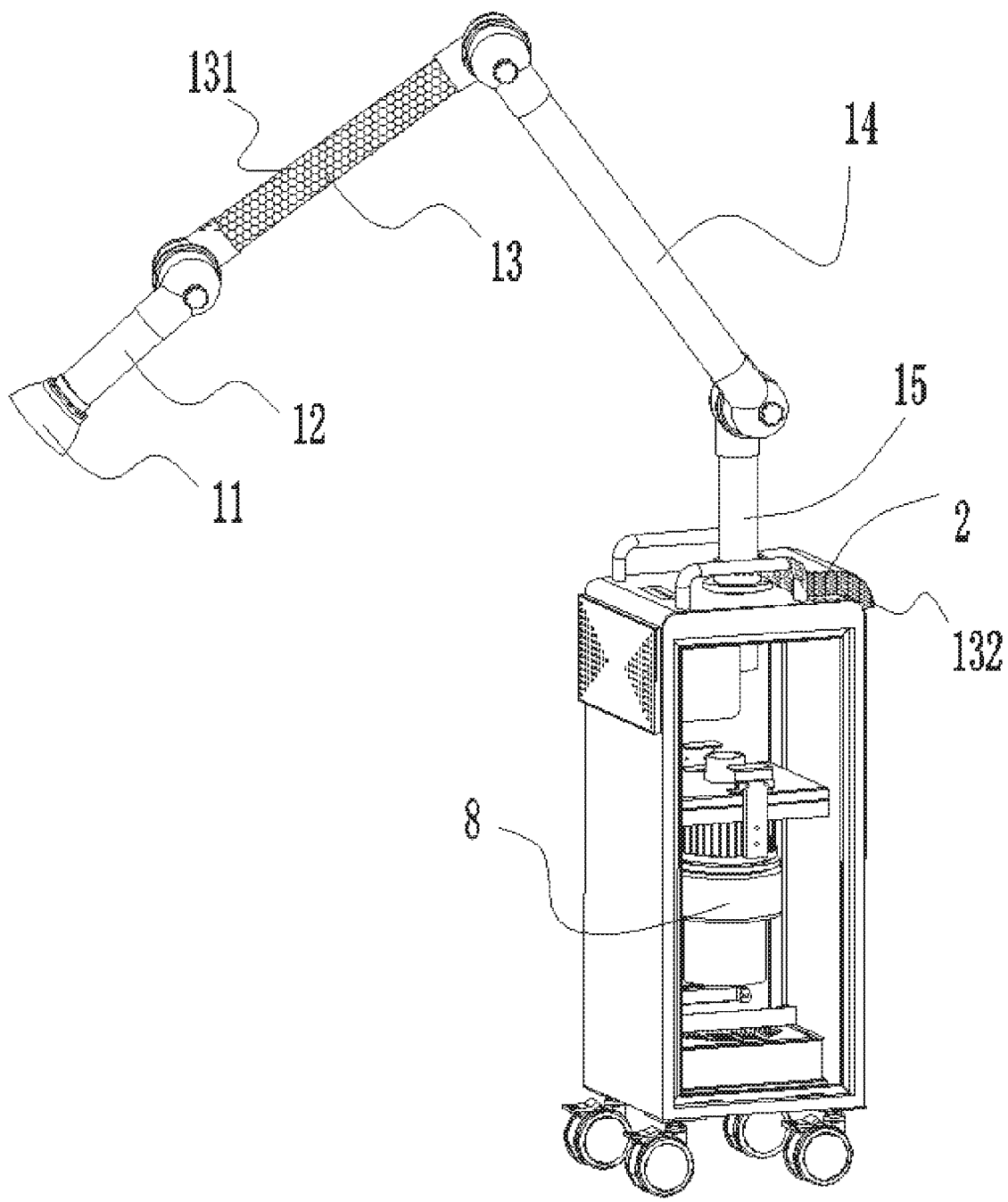
FIG. 3 is a schematic diagram showing the filter structures in the short arm and the air guide sleeve 3 according to the present invention.
Figure 4:
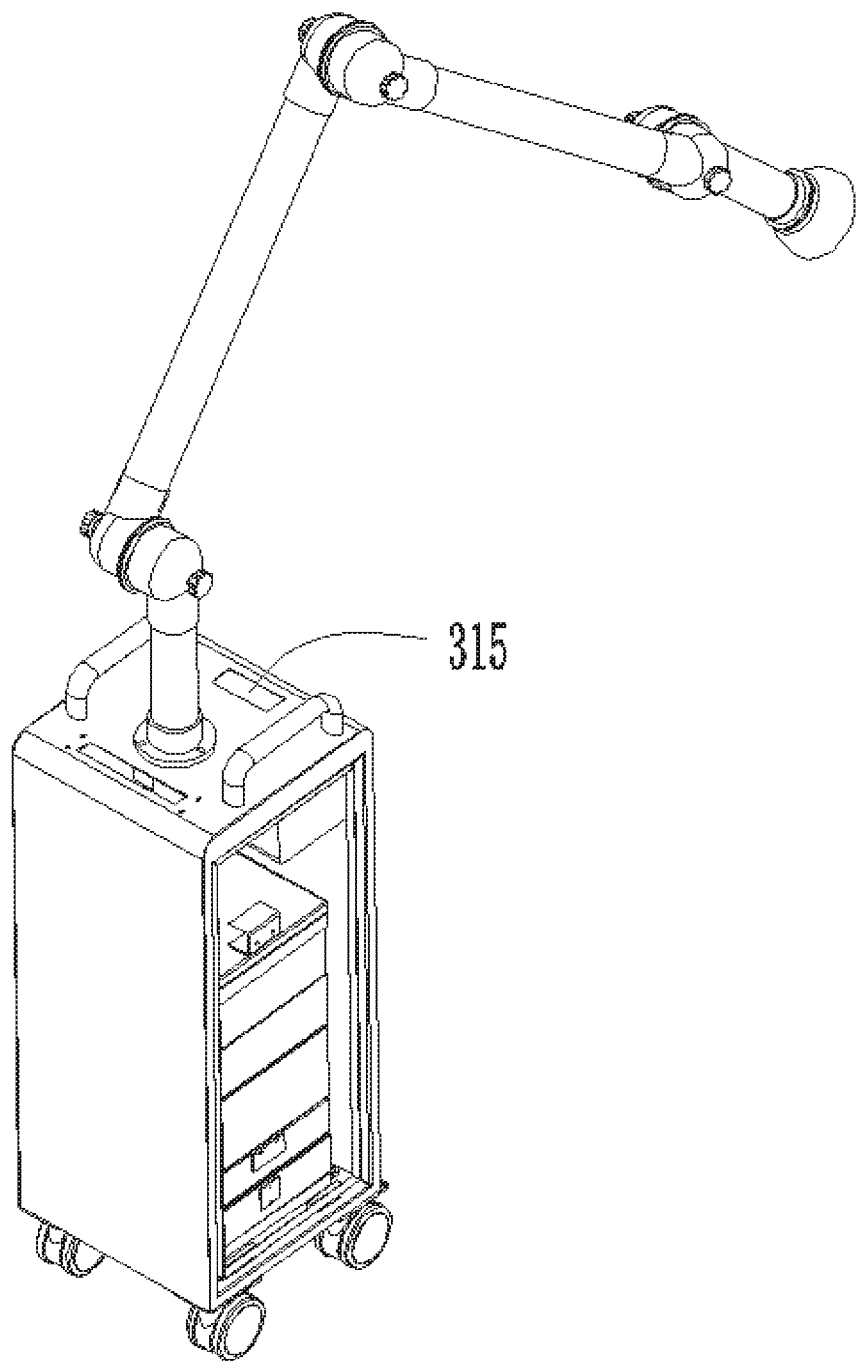
FIG. 4 is a schematic diagram showing the external structures of the present invention.
Figure 5:
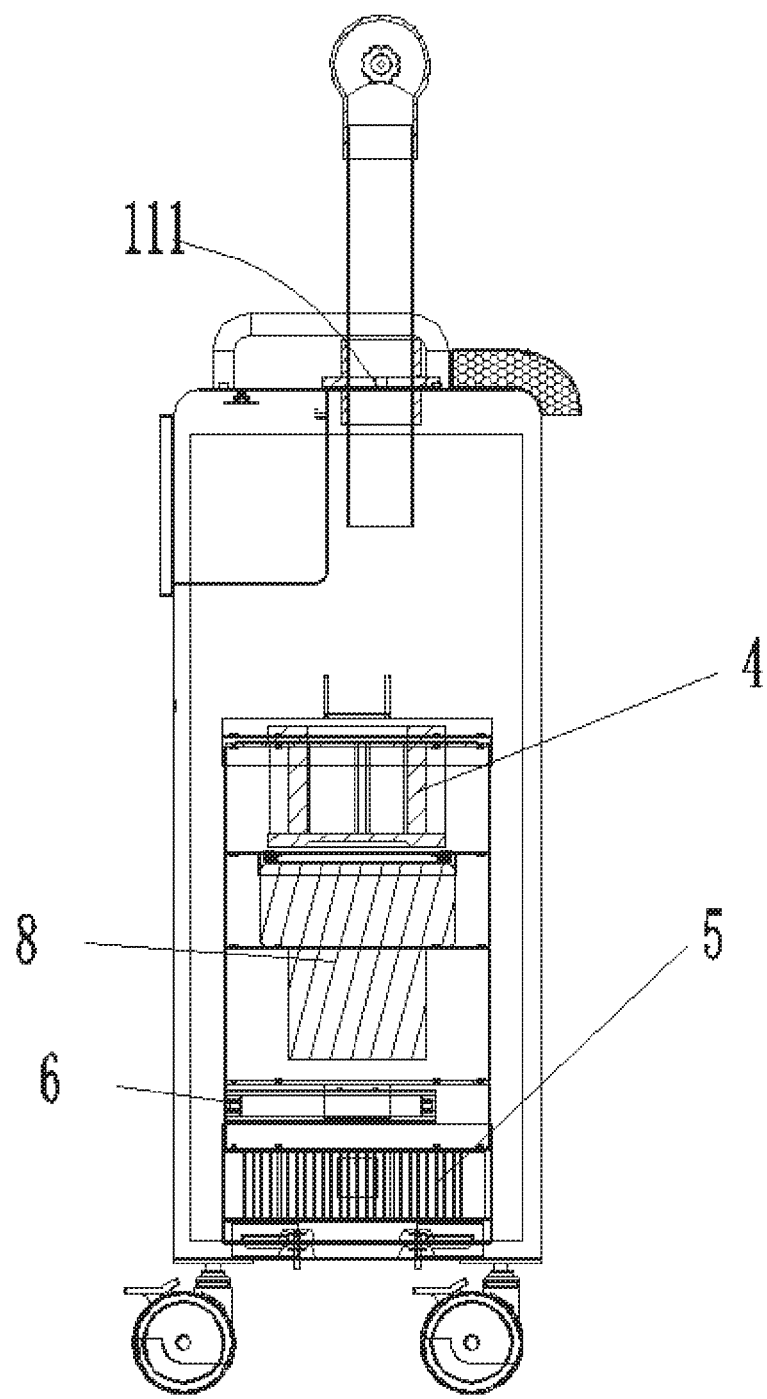
FIG. 5 is a cross-sectional view showing the structures of the present invention.

The technical solutions in the embodiments of the present invention will be described clearly and completely hereinafter with reference to the drawings. Obviously, the described embodiments are only part of the embodiments of the present invention, rather than all the embodiments. Based on the embodiments in the present invention, all other embodiments obtained by those skilled in the art without creative efforts shall fall within the scope of protection of the present invention.

In the description of the present invention, it should be noted that the position relationship indicated by the terminologies "upper", "lower", "inner", "outer", "front end", "rear end", "two ends", "one end" and "the other end" are based on the position relationship shown in the drawings, and is only intended to facilitate the description of the present invention and simplify the description, rather than indicating or implying that the device or element referred to must have a specific position and be constructed and operated in a specific direction. Therefore, the position relationship cannot be construed as a limitation to the present invention. In addition, the terminologies "first" and "second" are used only for descriptive purposes and cannot be construed as indicating or implying relative importance.

In the description of the present invention, it should be noted that, unless otherwise clearly specified and defined, the terminologies "install/arrange", "be provided with", "be connected", etc., should be understood in a broad sense. For example, the terminology "be connected" may indicate "be fixedly connected", "be detachably connected", "be integratedly connected", "be mechanically connected", "be electrically connected", "be directly connected", "be indirectly connected through an intermediate medium", or "internal connection between two components". For those skilled in the art, the specific meaning of the above terminologies in the present invention can be understood according to the specific circumstances.

As shown in FIGS. 1-16, a respiratory droplet electric suction device includes the suction arm 1 and the main body. The main body includes the housing, the air intake pipe 1, the fan 8, the filtering device 22, the muffling mechanism (73, 74, 75) and the exhaust mechanism 3. The suction arm 1 includes the first end and the second end. The second end is connected to the air intake port 111, and the first end is provided with the opening 11 for air admission. The air is pumped by the fan 8 to successively pass through the opening 11, the first end, the second end and the air intake port 111 into the main body. The fan 8, the filtering device 22 and the muffling mechanism (73, 74, 75) are all arranged in the housing. The air passes through the filtering device 22 and the muffling mechanism (73, 74, 75) and is then discharged through the exhaust mechanism 3. The exhaust mechanism 3 includes the exhaust port 315. The exhaust port 315 is arranged at the top of the housing and configured to discharge the air out of the top of the housing from the inside of the housing. In the respiratory droplet electric suction device of the present invention, the fan 8 provides kinetic energy to cause the air flow in the respiratory droplet electric suction device to flow in an orderly direction, and the suction generated at the opening 11 can quickly suck the nearby air flow into the housing. In use, the opening 11 is placed around the mouth of the oral disease patient to suck the air flow, so that the air flow between the doctor and the patient can be effectively pumped into the interior of the suction device for filtration and sterilization. Specifically, the particles, powder and water mist, or vapor, produced during the oral surgery can be collected, and then filtered and sterilized many times to avoid the cross-infection caused by the bacteria and viruses and ensure safety, sterility, and no infection during the oral surgery.

As shown in FIGS. 6-10, in order to effectively control the discharge direction of the air after being sterilized, the exhaust mechanism 3 is provided with a plurality of deflectors (31, 32, 33, 34) configured to guide the air flow. The air flow is guided by the plurality of deflectors (31, 32, 33, 34) to be discharged out of the top of the housing from the inside of the housing. The plurality of deflectors (31, 32, 33, 34) can be linked to one another. The linkage mentioned above can be realized by connecting the plurality of deflectors together via a connecting rod or a motor to realize synchronous swing. The inclination of the deflectors (31, 32, 33, 34) can be adjusted manually and/or automatically. The deflectors (31, 32, 33, 34) include the transverse deflectors (31, 32, 33, 34) and the longitudinal deflectors (31, 32, 33, 34). The transverse deflectors (31, 32, 33, 34) can adjust the discharge direction of the air along the transverse direction, and the longitudinal deflectors (31, 32, 33, 34) can adjust the discharge direction of the air flow along the longitudinal direction. It should be noted that the transverse direction and longitudinal direction here are only intended to facilitate the description of the structure rather than to define the function and direction of the structure.

The transverse deflectors (31, 32, 33, 34) and the longitudinal guide plates (31, 32, 33, 34) are interlaced with each other. The deflectors include the left deflectors (31, 32, 33, 34) and the right deflectors (31, 32, 33, 34). The angle of the left deflectors (31, 32, 33, 34) and the angle of the right deflectors (31, 32, 33, 34) can be adjusted, respectively. Similarly, the deflectors can also include the upper deflectors and the lower deflectors. The terminologies "upper", "lower", "left" and "right" mentioned above are intended to facilitate the illustration of the structure and should not be construed as limiting the present invention. Several exemplary embodiments of the deflectors are shown in FIGS. 6-10 the drawings.

Figure 6:
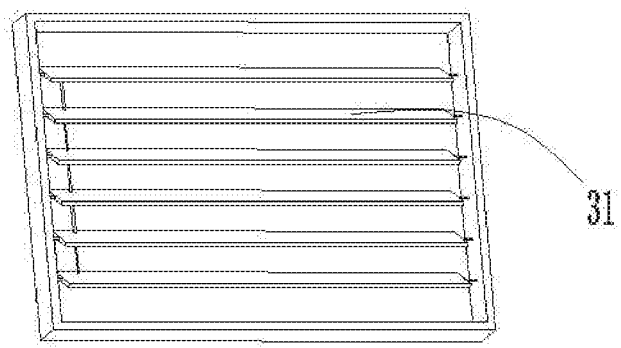
FIG. 6 is a schematic diagram showing the first embodiment of the structure of the deflector according to the present invention.

As shown in the embodiment of FIG. 6, a plurality of deflectors are arranged, and the plurality of deflectors are connected by a connecting rod. When the angle of one deflector is adjusted, the angle of the other deflectors is synchronously adjusted.

Figure 7:
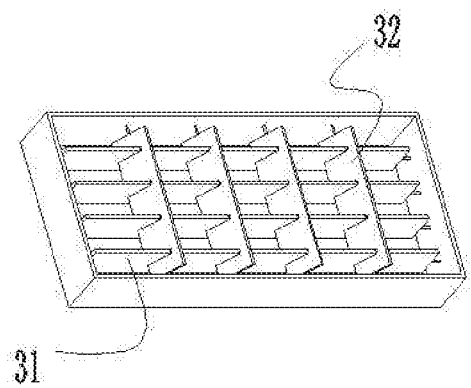
FIG. 7 is a schematic diagram showing the second embodiment of the structure of the deflector according to the present invention.

As shown in the embodiment of FIG. 7, the direction of the transverse deflectors is fixed, and the angle of the longitudinal deflectors can be adjusted.

Figure 8:
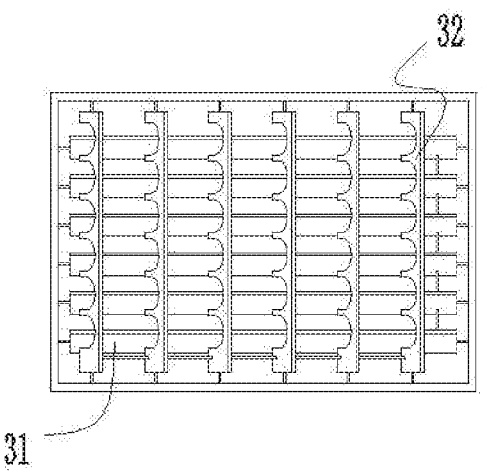
FIG. 8 is a schematic diagram showing the third embodiment of the structure of the deflector according to the present invention.

As shown in the embodiment of FIG. 8, both the angle of the transverse deflectors and the angle of the longitudinal deflectors can be adjusted.

Figure 9:
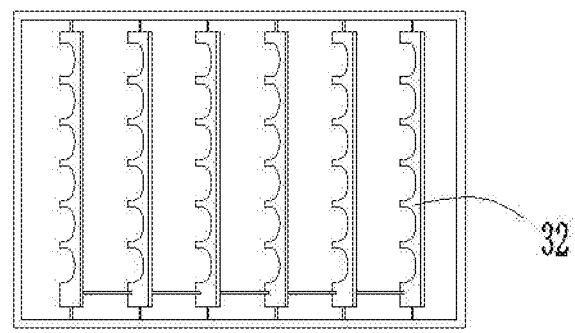
FIG. 9 is a schematic diagram showing the fourth embodiment of the structure of the deflector according to the present invention.

As shown in the embodiment of FIG. 9, the angle of the deflectors is adjusted along the transverse direction.

Figure 10:
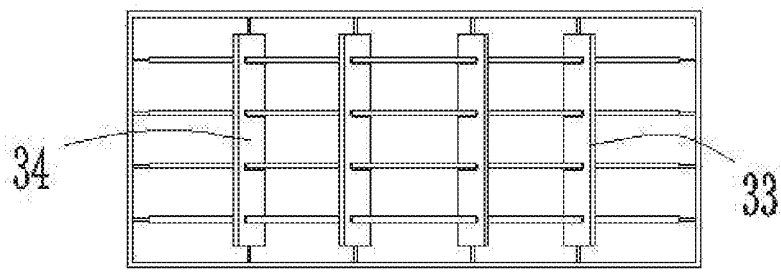
FIG. 10 is a schematic diagram showing the fifth embodiment of the structure of the deflector according to the present invention.
Figure 11:
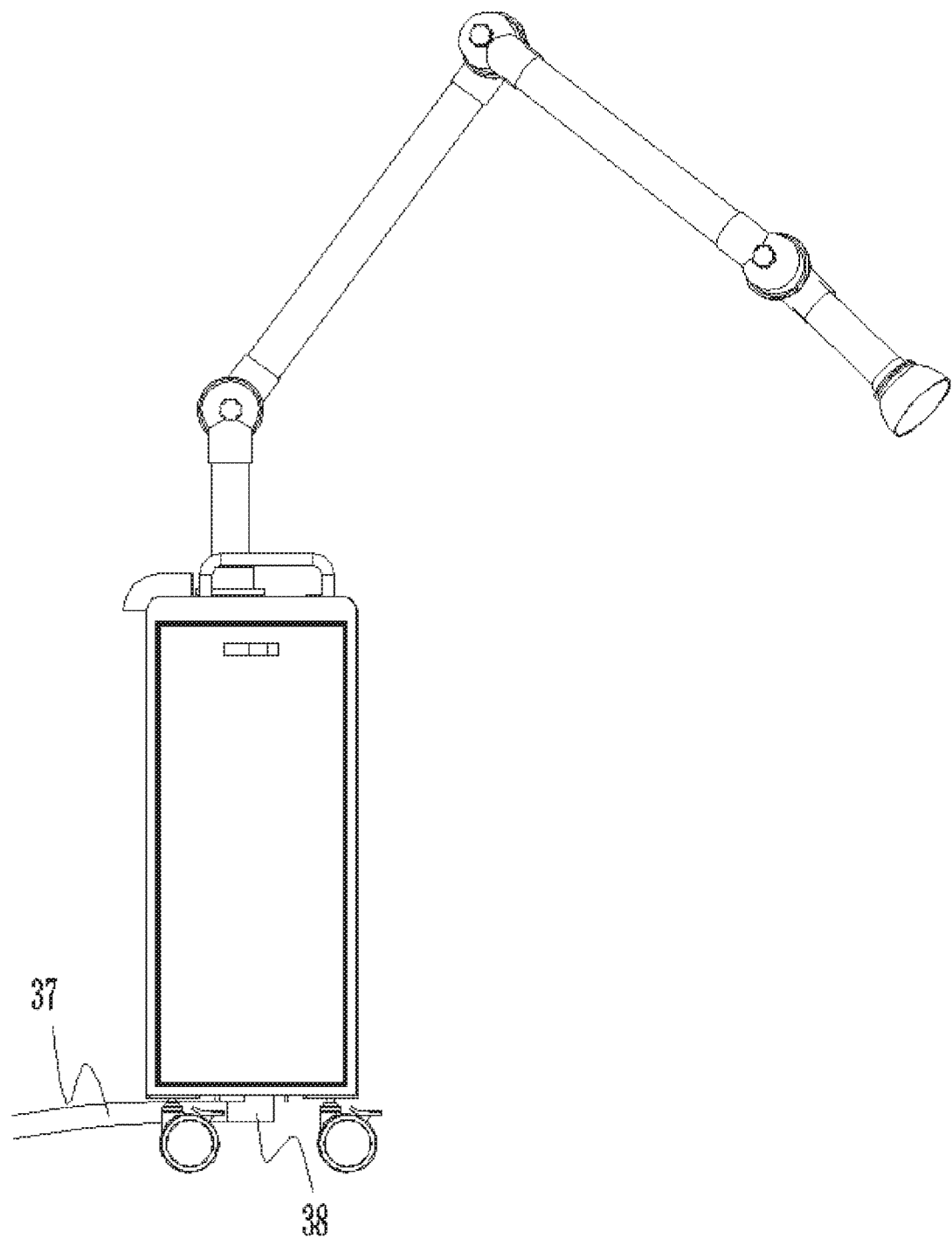
FIG. 11 is a schematic diagram showing the first embodiment of the structure of the exhaust pipe according to the present invention.
Figure 12:
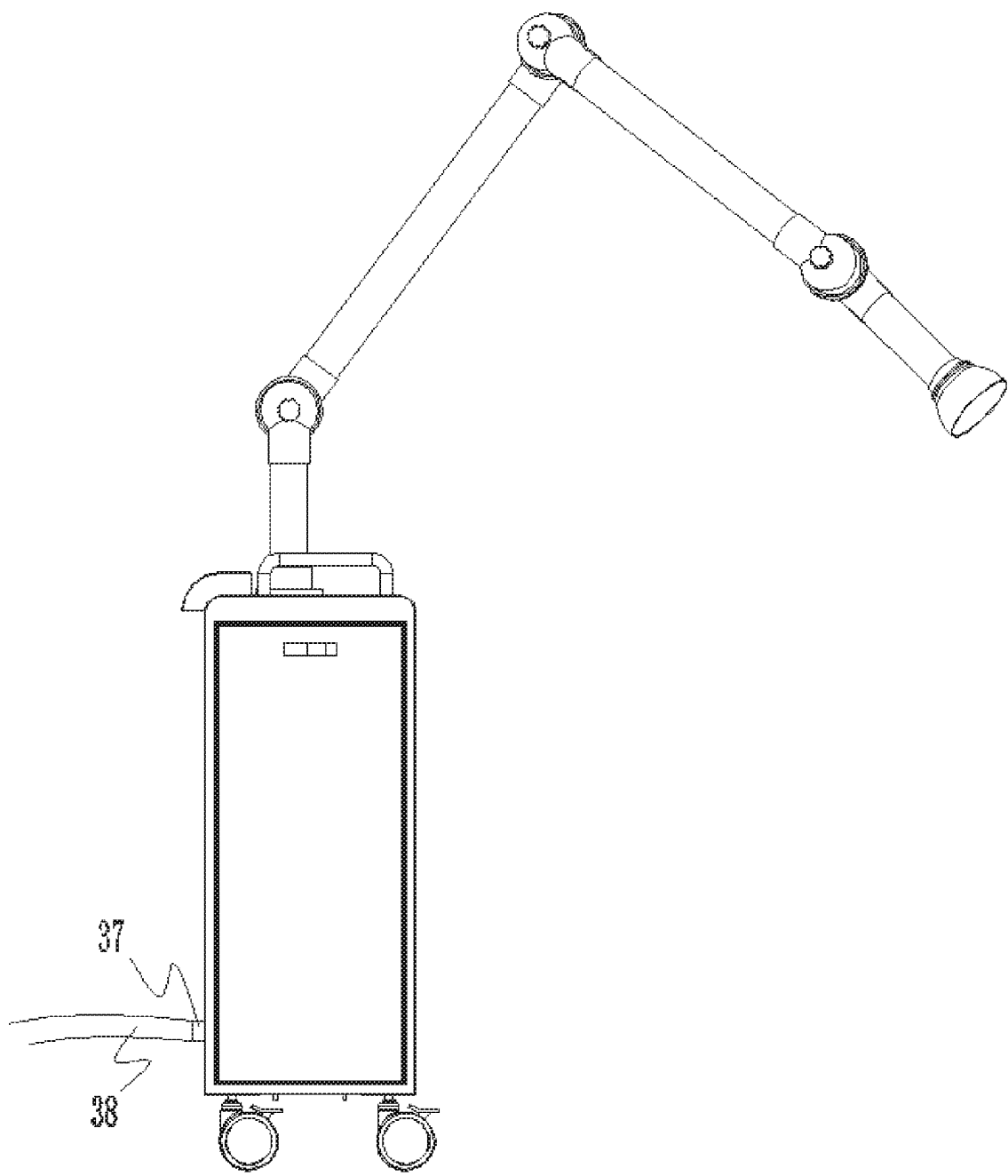
FIG. 12 is a schematic diagram showing the second embodiment of the structure of the exhaust pipe according to the present invention.

As shown in the embodiment of FIG. 10, the deflectors include the left deflectors and the right deflectors, and the angle of the left deflectors and the angle of the right deflectors can be adjusted along the transverse direction. The left deflectors can be linked to one another, and the right deflectors can be linked to one another. Similarly, the angle of the deflectors can be synchronously adjusted along the longitudinal direction and the transverse direction, respectively, or the angle of a part of the deflectors can be adjusted along the longitudinal direction and the transverse direction, respectively.

The above embodiments are only examples of the implementation mode and should not be construed as the exhaustion of examples of the present invention, and other similar technical solutions realized without intelligent labor should be construed as the spirit of the present invention.

The deflectors (31, 32, 33, 34) are arranged in the exhaust port 315, and the air guide sleeve 35 is arranged above the exhaust port 315. The air guide sleeve 35 extends upward from the top of the housing.

The air guide sleeve 35 extends upward in a certain degree of curvature.

The air guide sleeve 35 guides the air flow to flow from the top of the housing to the side wall of the housing to discharge the air flow downward.

The air guide sleeve 35 is a guide cavity with freely adjustable curvature. In use, the air guide sleeve can discharge the air flow by adjusting the direction of the exhaust port at the front end of the air guide sleeve 35.

Figure 13:
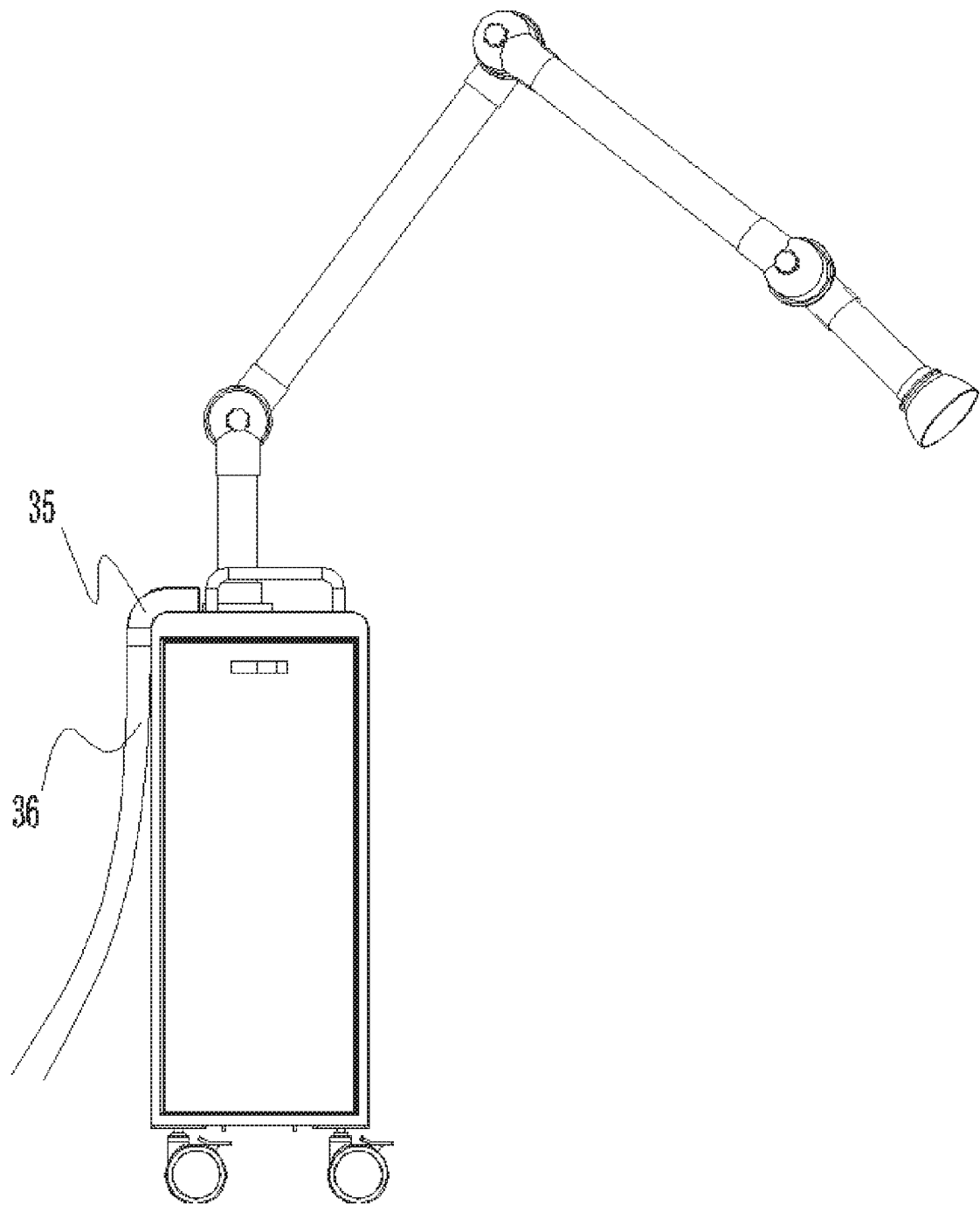
FIG. 13 is a schematic diagram showing the third embodiment of the structure of the exhaust pipe according to the present invention.
Figure 14:
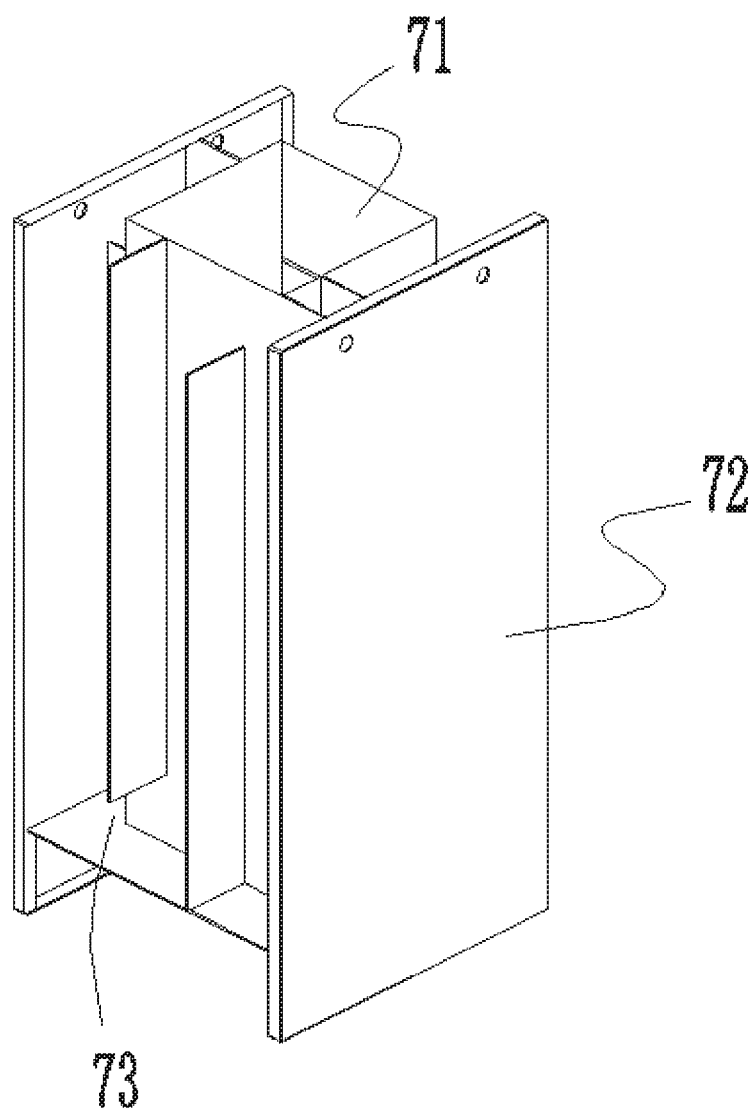
FIG. 14 is a schematic diagram showing the structure of the sound insulation mechanism according to the present invention.
Figure 15:
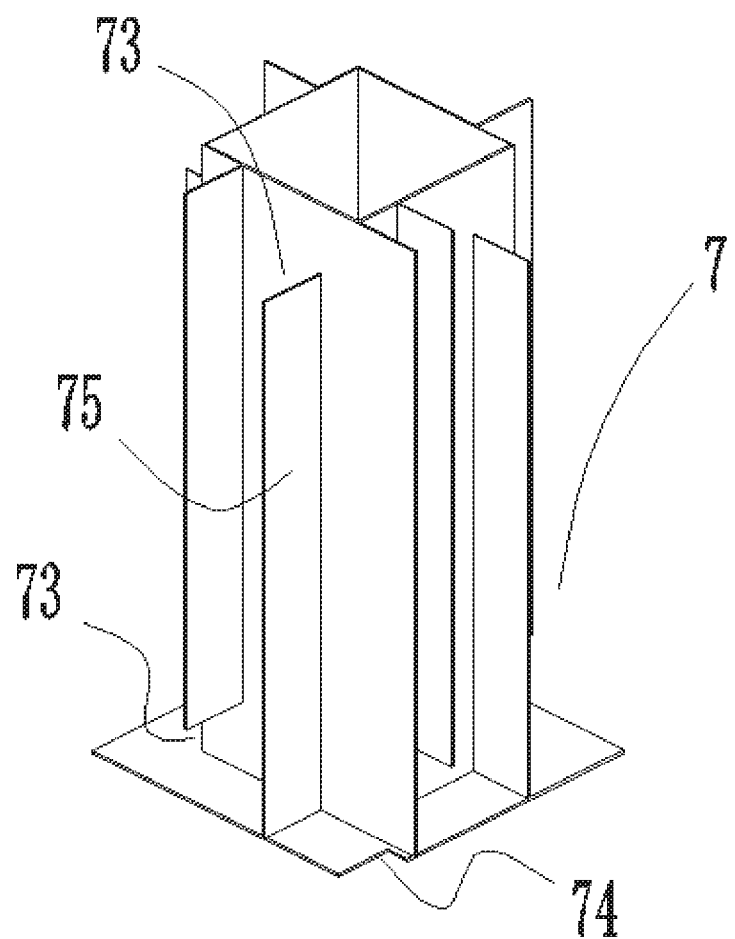
FIG. 15 is a schematic diagram showing the structure of the sound insulation mechanism at the outside of the inner liner according to the present invention.
Figure 16:
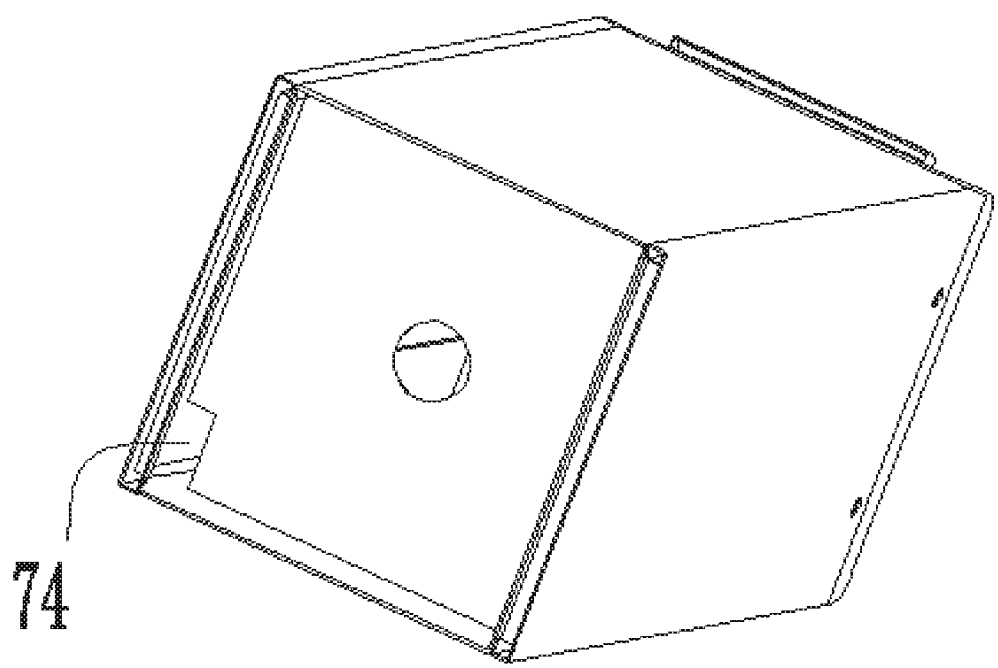
FIG. 16 is a schematic diagram showing the bottom ventilation structure of the sound insulation mechanism according to the present invention.

As shown in FIGS. 13, the suction device provided by the present invention further includes the first guide pipe 36, and the first guide pipe 36 can be connected to the air guide sleeve 35. The air guide sleeve guides the air flow to flow from the top of the housing to the side wall of the housing to discharge the air flow downward, and the filter cotton 132 is arranged in the air guide sleeve. The filter cotton arranged in the air guide sleeve can filter the inhaled air flow for the last time, and play the role in sound insulation and insulation of the external air and so on.

The suction arm 1 includes the fixed arm 15 arranged vertically and fixed on the upper portion of the housing, the long arm 14 pivotally connected to the other end of the fixed arm 15, the short arm 13 pivotally connected to the other end of the long arm 14, and the positioning arm 12 pivotally connected to the short arm 13. The opening 11 is arranged at the front end of the positioning arm 12, and the opening 11 has a incrementally decreasing size toward one end of the positioning arm 12. The filter cotton 131 is arranged in the short arm. The filter cotton arranged in the short arm performs the first filtration for mainly filtering the powder, water and other large particles produced during the procedure. The suction arm 1 can be rotated at any angle to perform positioning, and this multi-angle adjustment can be realized by the arms with different lengths.

The housing includes the inner liner 71 and the shell 72. The upper portion of the shell 72 is provided with the top tray 201. The fan 8 and the filtering device 22 are arranged in the inner liner 71. The air flows out of the lower end of the inner liner 71 from the upper end of the inner liner 71, and then flows into the muffling mechanism (73, 74, 75), and then the air is discharged through the exhaust mechanism 3 arranged on the top tray 201 of the housing. The filtered air is sterilized.

As shown in FIGS. 14-18, the inner liner 71 is arranged in the muffling mechanism. The muffling mechanism is additionally provided with circuitous routes (73, 74, 75) to maximize the muffling effect.

The ultraviolet sterilization box is arranged in the inner liner 71. The High Efficiency Particulate Air 222 (HEPA222) and the ultraviolet sterilization lamp 231 are arranged in the ultraviolet sterilization box, and the ultraviolet sterilization lamp 231 irradiates on the HEPA222. The ultraviolet sterilization lamp 231 is arranged on the side wall of the ultraviolet sterilization box. Bacteria and viruses are intercepted by the HEPA and inactivated by the ultraviolet light.

The shell includes a shell frame and a side wall. A multi-stage flanging is arranged at the connection between the shell frame and the side wall, and the sound insulation cotton is arranged on the flanging.

The sound insulation cotton with a concave portion and a convex portion is arranged on the outer wall of the inner liner 71 and the inner wall of the shell.

The suction device further includes the second exhaust pipe 38 and the second exhaust mechanism 37. The second exhaust mechanism 37 is arranged at the bottom or the side wall of the housing, and the second exhaust pipe 38 is connected to the second exhaust mechanism 37. At least one group of the group consisting of the second exhaust pipe 38 and the second exhaust mechanism 37 and the group consisting of the exhaust pipe and the exhaust mechanism 3 is arranged.

As shown in FIGS. 17-33, the filtering device of the present invention includes the bacteria filtering mechanism 5 arranged modularly. The ultraviolet sterilization lamp 6 for inactivating bacteria cooperates with the bacteria filtering screen 53 in the following manner. Firstly, the air flowing into the bacteria filtering mechanism 5 is filtered by the bacteria filtering screen 53, and then the bacteria filtered and accumulated on the surface of the bacteria filtering screen 53 are continuously irradiated by the ultraviolet sterilization lamp 6 to be sterilized. The filtering device includes the air inlet end 121 and the exhaust end 58. The bacteria filtering mechanism 5 is arranged between the air inlet end 121 and the exhaust end 58. The bacteria filtering screen 53 for adsorbing bacteria and the ultraviolet sterilization lamp 6 for inactivating the bacteria are arranged in the bacteria filtering mechanism 5. The bacteria filtering mechanism 5 includes the first side wall 571 and the second side wall 561. The first side wall 571 is connected to the air inlet end 121, and the second side wall 561 is connected to the exhaust end 58. The air entering from the first side wall 571 is filtered by the bacteria filtering screen 53 and then discharged by the second side wall 561. The ultraviolet sterilization lamp 6 is arranged corresponding to the bacteria filtering screen 53. In the present invention, the bacteria filtering mechanism 5 is configured to inactivate the collected bacteria, wherein the large particles and vapor solution is filtered at the front end to realize primary filtration, and the bacteria are filtered at the rear end, that is, filtered in the filtering device and inactivated by the ultraviolet light. The air inlet end 121 is connected to the air intake port 111, and the exhaust end is connected to the exhaust port 315.

As shown in FIGS. 17-31, as a preferred embodiment, the bacteria filtering screen 53 includes the windward surface. The irradiation cavity is arranged between the first side wall 571 and the bacteria filtering screen 53. The ultraviolet light of the ultraviolet sterilization lamp 6 is scattered on the windward surface through the irradiation cavity. A certain distance is reserved between the ultraviolet sterilization lamp 6 and the bacteria filtering screen 53 to facilitate the uniform irradiation of the ultraviolet sterilization lamp. After being filtered, the bacteria are mainly collected on the windward surface. The windward surface is arranged corresponding to the ultraviolet sterilization lamp, which can effectively improve the sterilization efficiency of the ultraviolet sterilization lamp.

Figure 17:
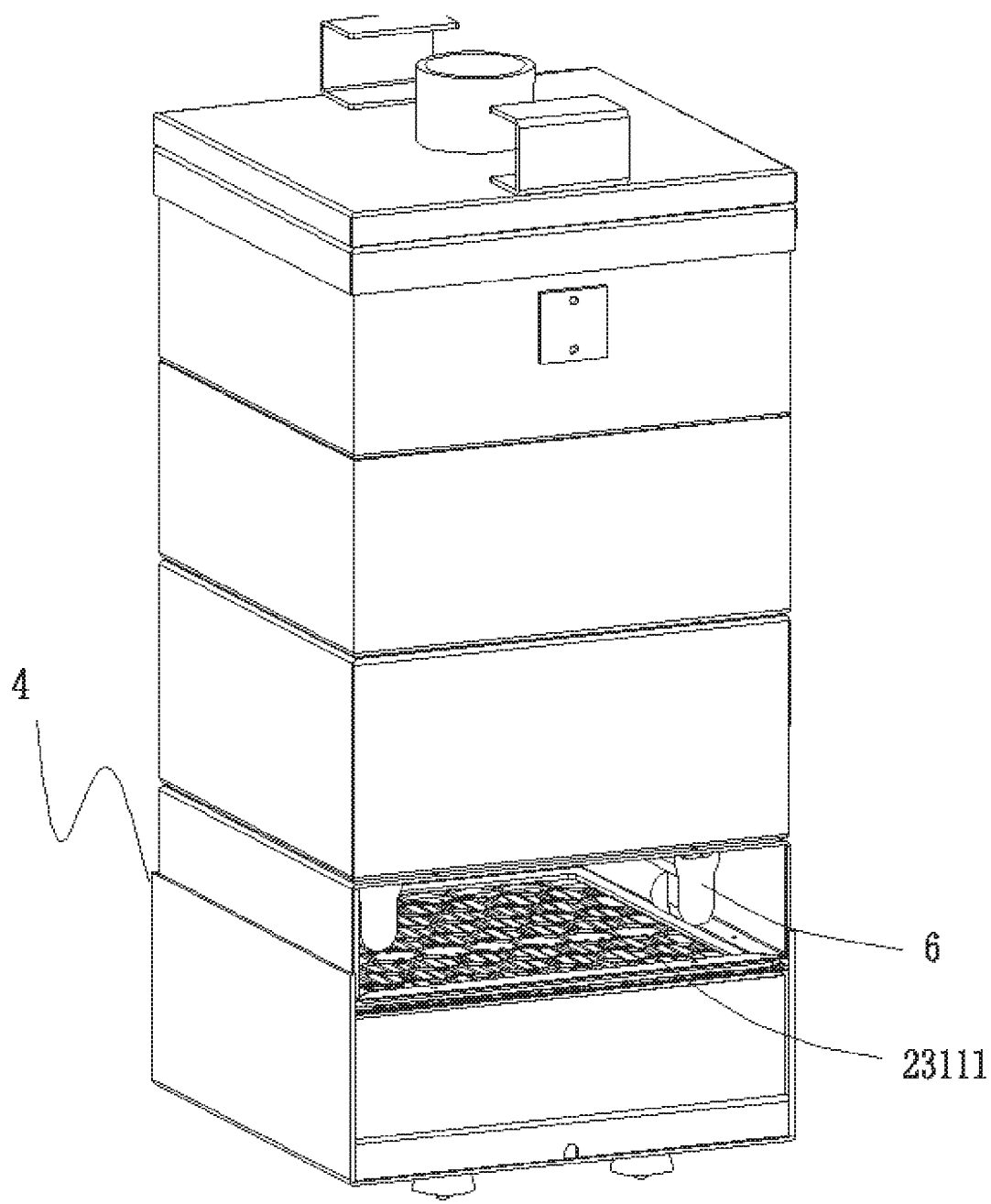
FIG. 17 is a schematic diagram showing the structures of the air intake and the filtering device according to the present invention.
Figure 18:
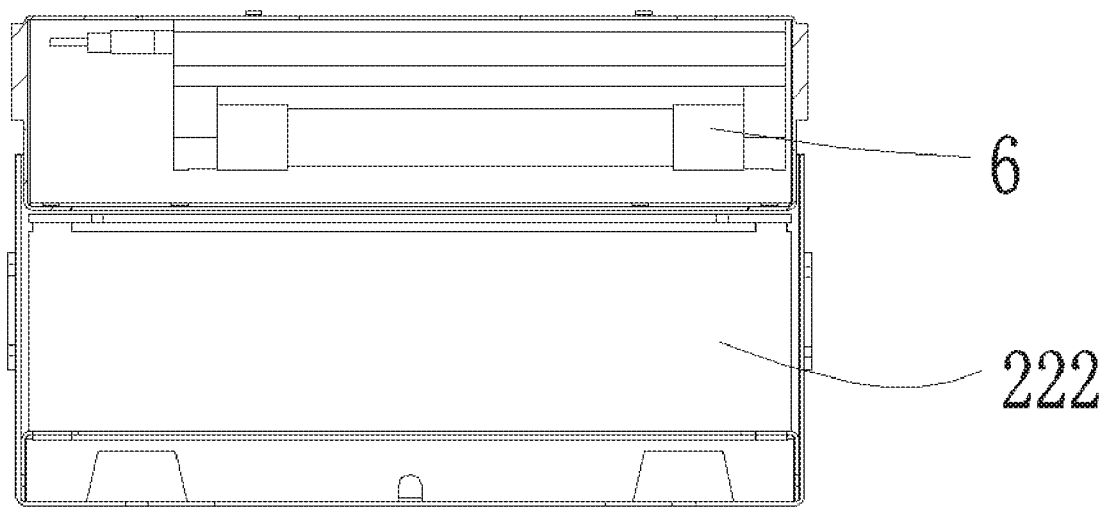
FIG. 18 is a cross-sectional view of the structure of the filtering device.
Figure 19:
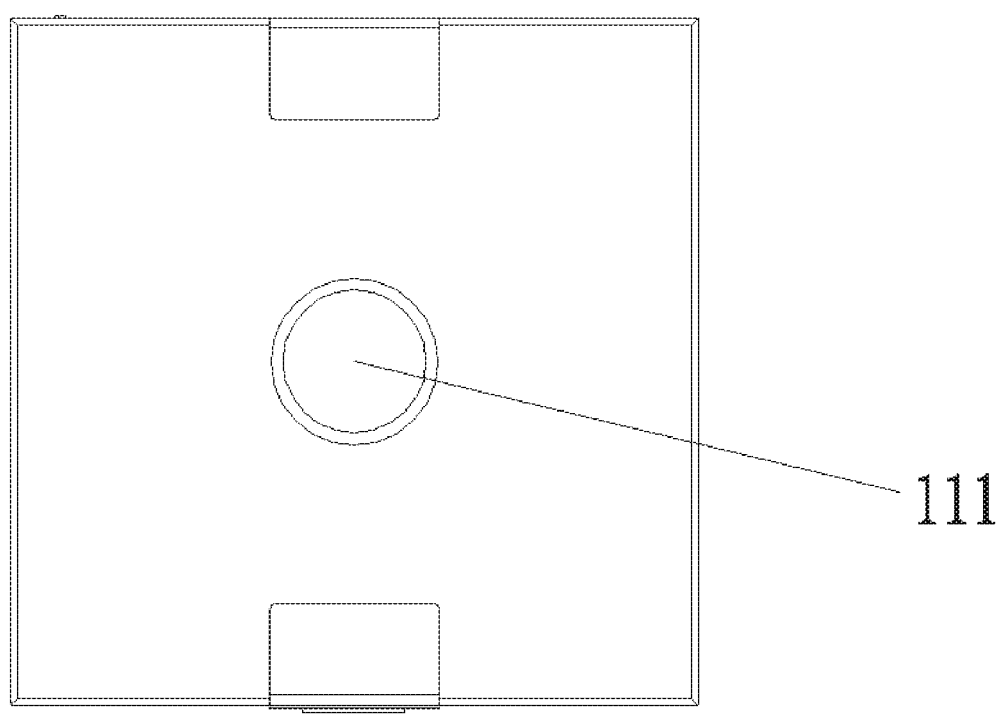
FIG. 19 is a schematic diagram showing the structure of the exhaust end of the filtering device.
Figure 28:
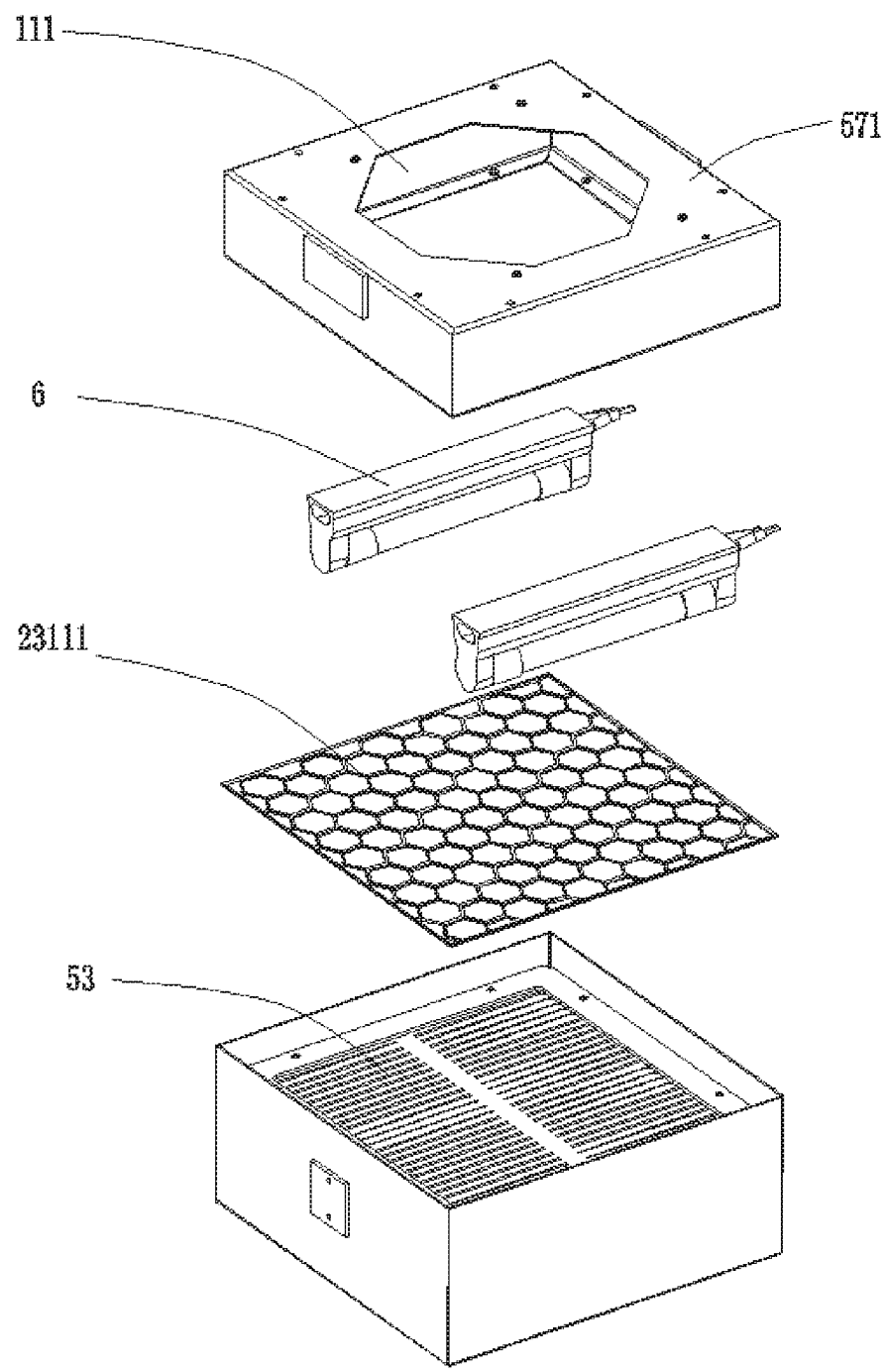
FIG. 28 is a schematic diagram of the structure of the suction device with the photocatalyst.

As shown in FIGS. 17 and 28, as a preferred embodiment, the photocatalyst 23111 is arranged in the irradiation cavity, and the photocatalyst 23111 is arranged between the ultraviolet sterilization lamp 6 and the irradiation cavity. The photocatalyst 23111 is additionally arranged to decompose the toxins released by bacteria or fungi into harmless components and has the functions of removing formaldehyde, deodorizing, anti-fouling, purifying air and others. As a preferred embodiment, the photocatalyst 23111 is arranged in the irradiation cavity, and the photocatalyst 23111 is arranged between the ultraviolet sterilization lamp 6 and the irradiation cavity.

As shown in FIG. 28, as a preferred embodiment, the photocatalyst 23111 is a titanium dioxide mesh structure. More preferably, the photocatalyst 23111 is a mesh titanium dioxide photocatalyst, which not only ensures the luminous flux of the ultraviolet light, but also realizes the functions of removing formaldehyde, deodorizing, anti-fouling, purifying air and others through the photocatalyst 23111.

As shown in FIG. 28, as a preferred embodiment, the photocatalyst 23111 is arranged above the filtering screen. The photocatalyst 23111 can reflect the ultraviolet light to enhance the sterilization performance of the ultraviolet light. The photocatalyst 23111 is arranged above and close to the filtering screen. The ultraviolet light irradiates on the photocatalyst 23111 and is then reflected by the photocatalyst 23111, which effectively improves the inactivation efficiency of the bacteria via the ultraviolet light.

Figure 29:
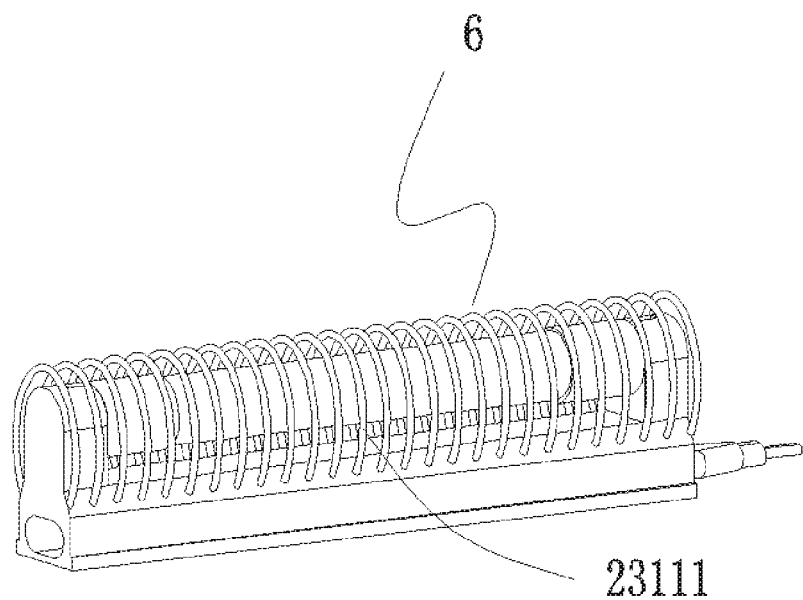
FIG. 29 is a schematic diagram of the structure of the ultraviolet sterilization lamp with the photocatalyst from the first angle of view.
Figure 30:
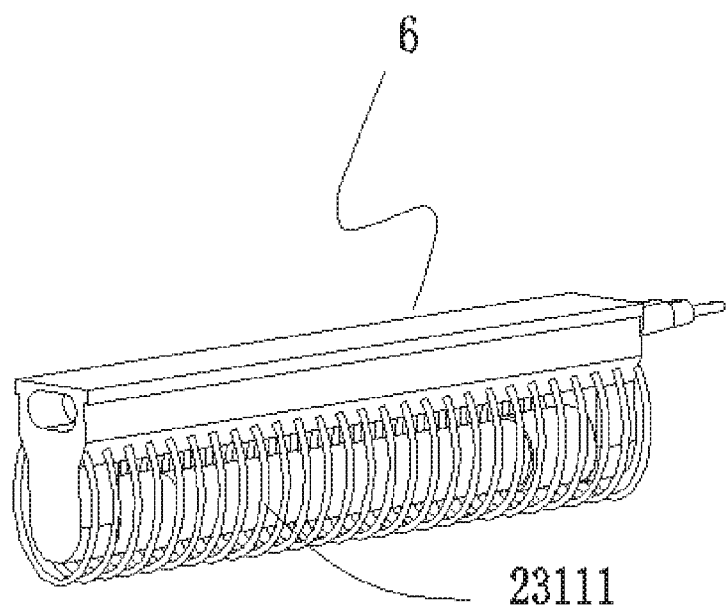
FIG. 30 is a schematic diagram of the structure of the ultraviolet sterilization lamp with the photocatalyst from the second angle of view.
Figure 31:
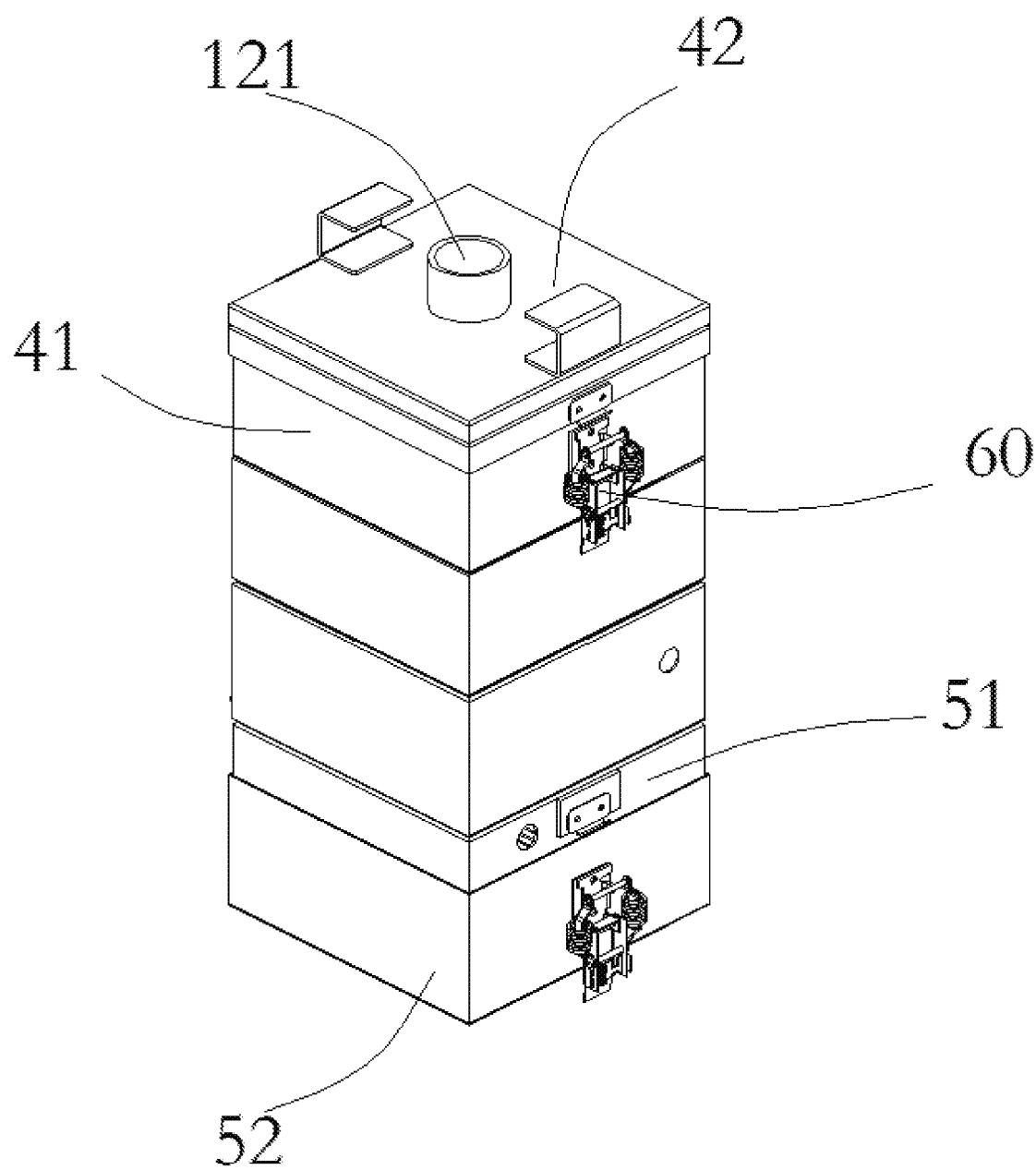
FIG. 31 is a schematic diagram of the structure of the filtering device.
Figure 32:
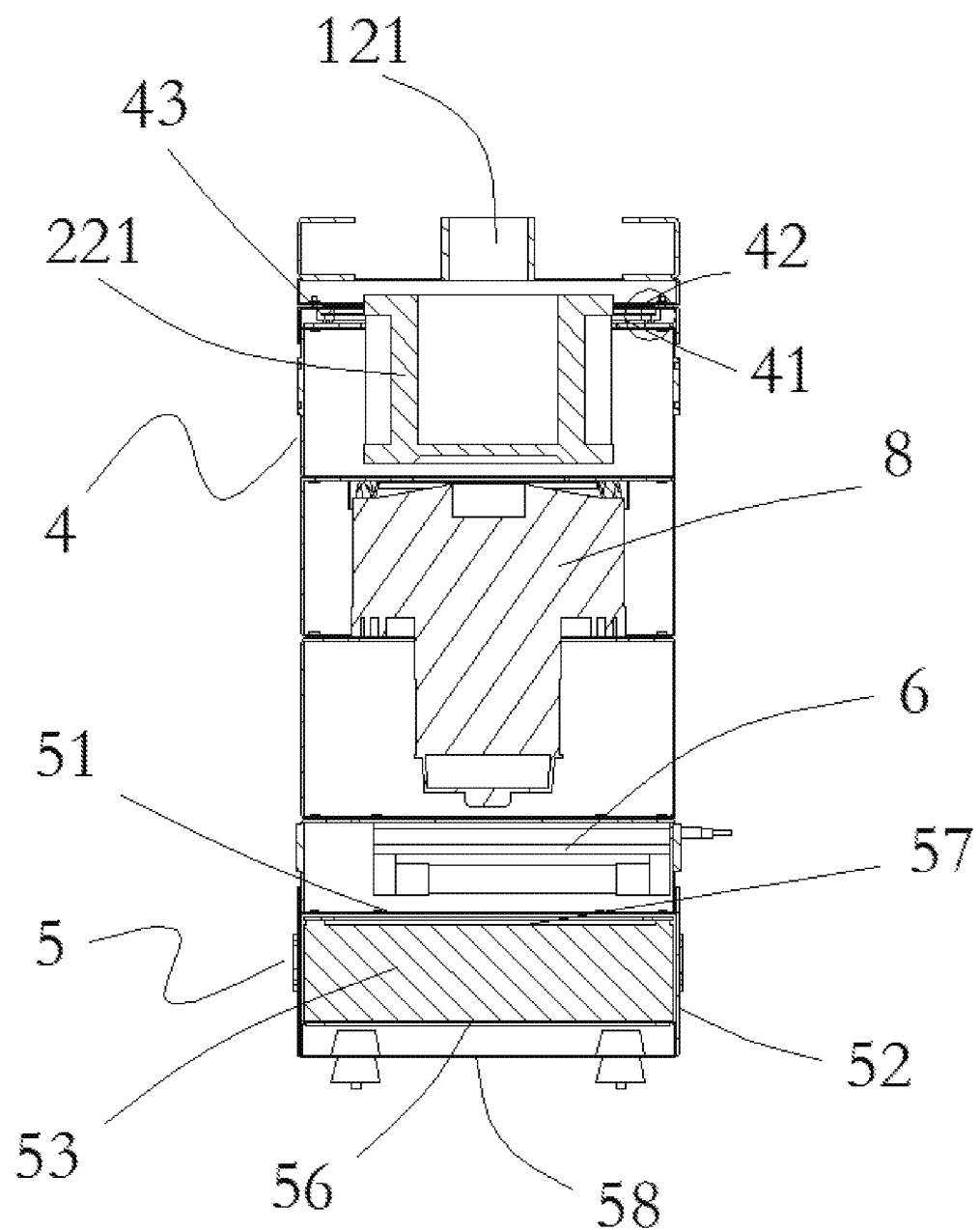
FIG. 32 is a cross-sectional view of the structure of the filtering device.
Figure 33:
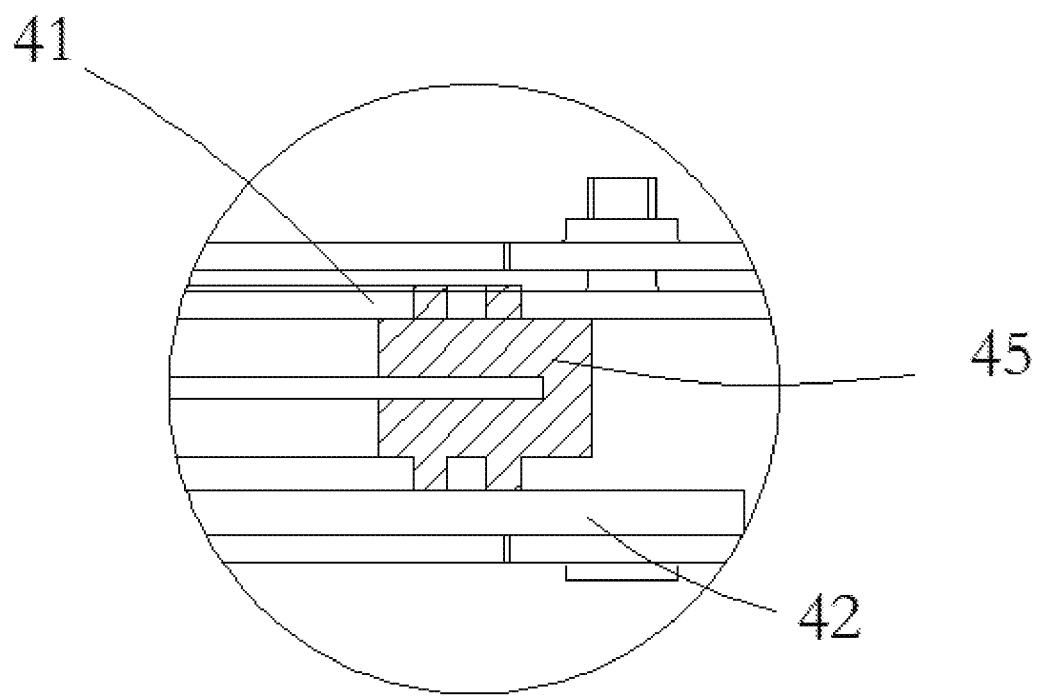
FIG. 33 is a schematic diagram of the structure of the sealing soft material.
Figure 34:
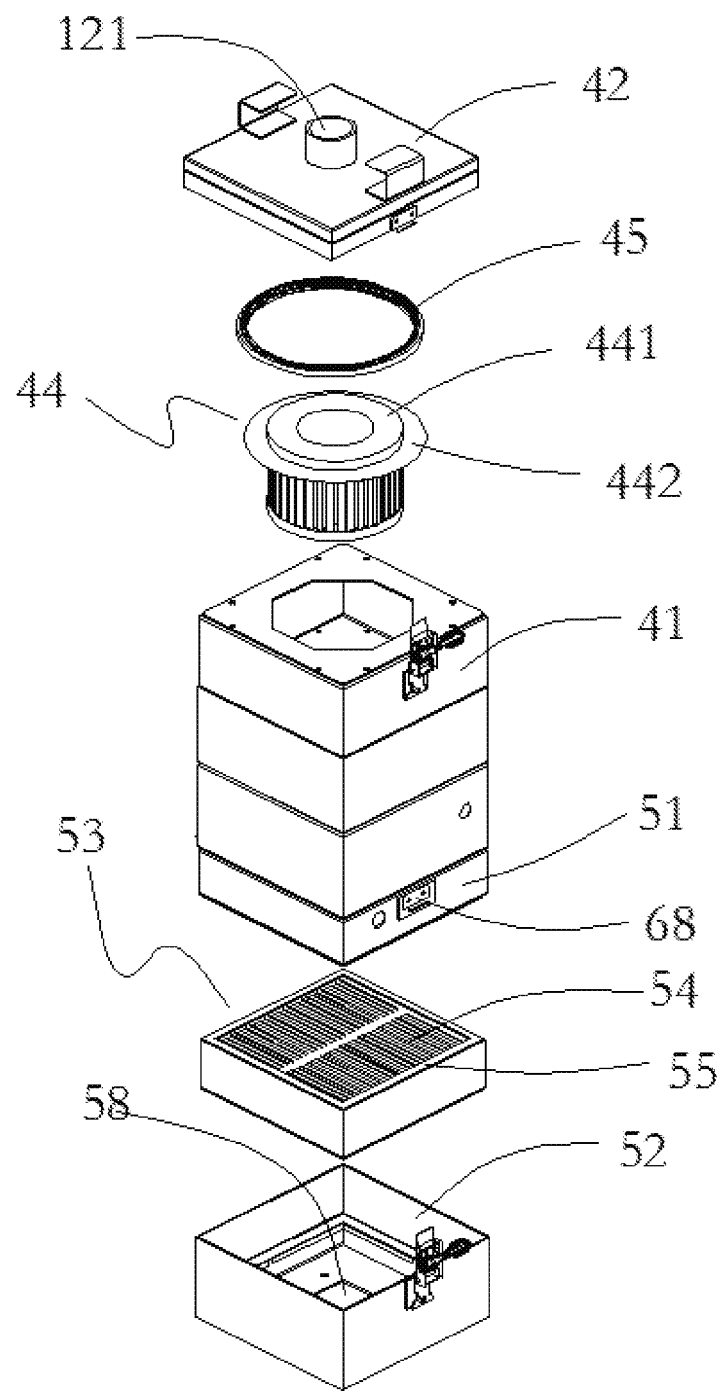
FIG. 34 is an exploded view showing the structures of the filtering device.
Figure 35:
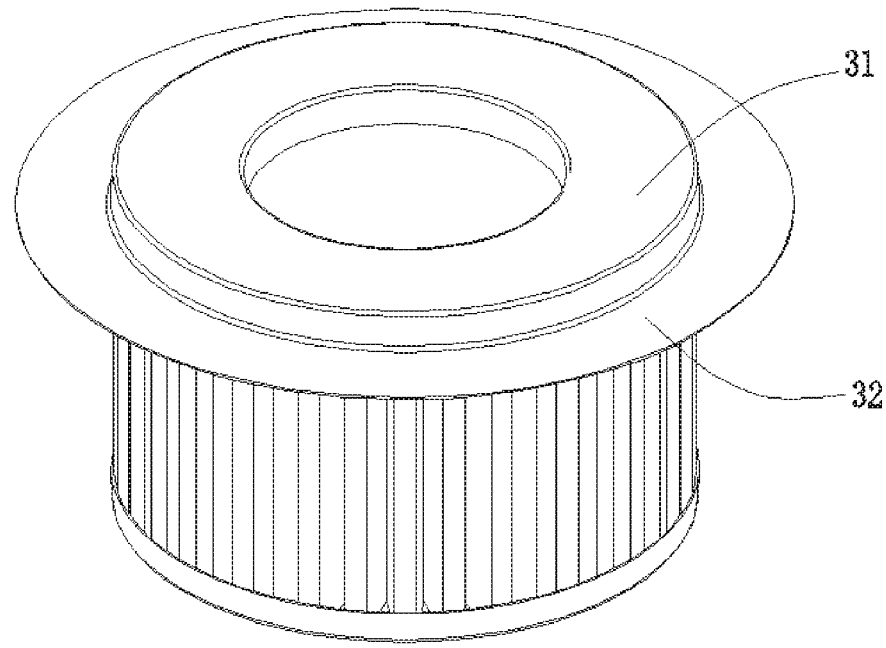
FIG. 35 is a schematic diagram of the structure of the front filtering screen.
Figure 36:
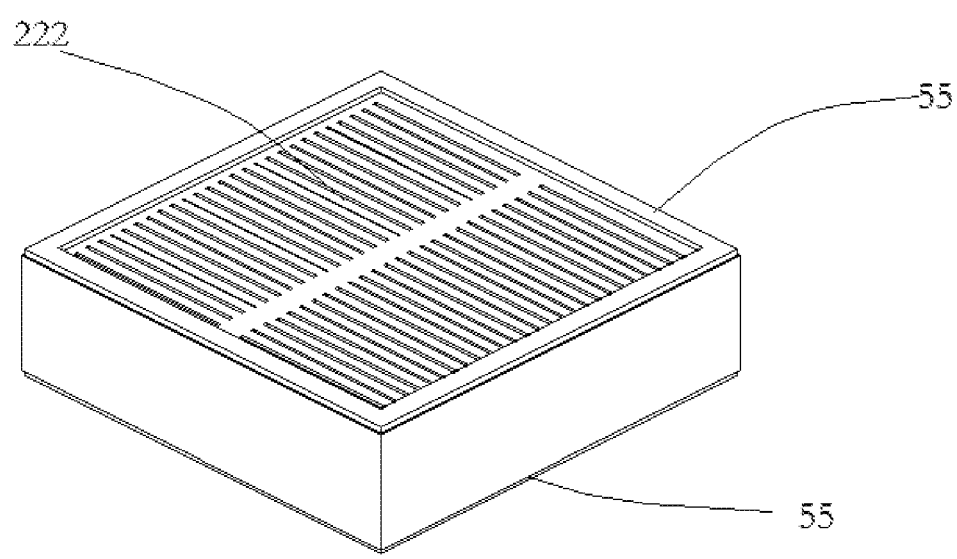
FIG. 36 is a schematic diagram of the structure of the bacteria filtering screen.
Figure 37:
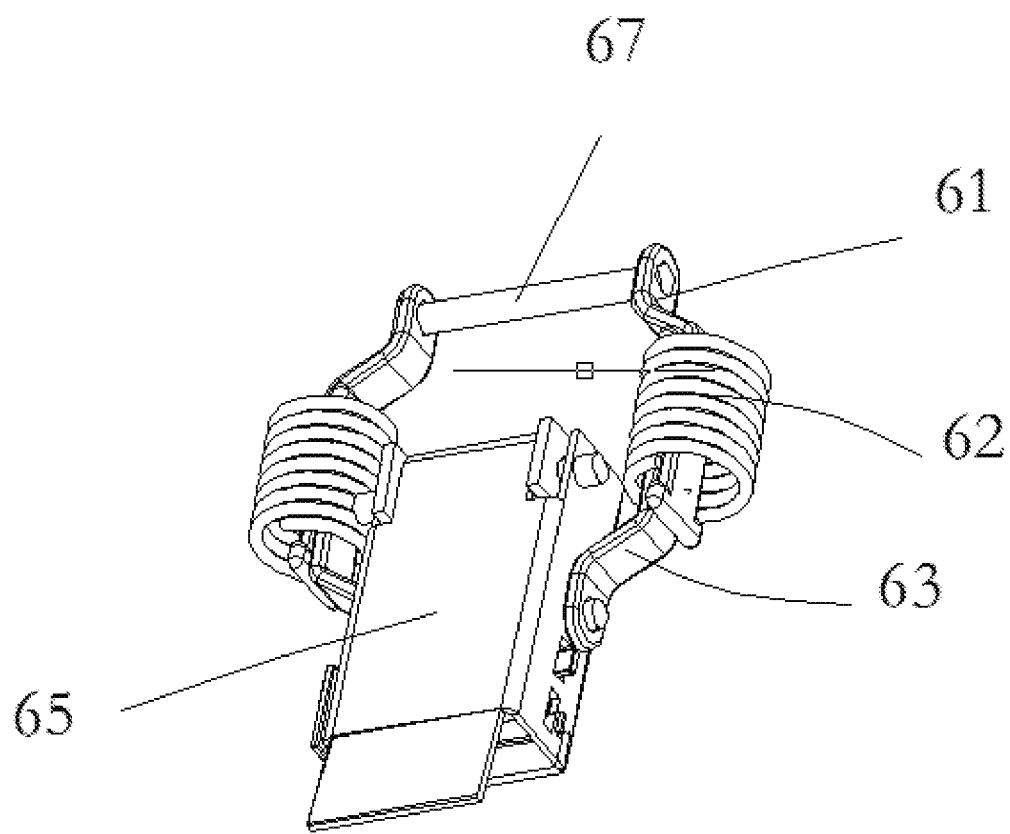
FIG. 37 is a schematic diagram of the structure of the spring lock from the first angle of view.
Figure 38:
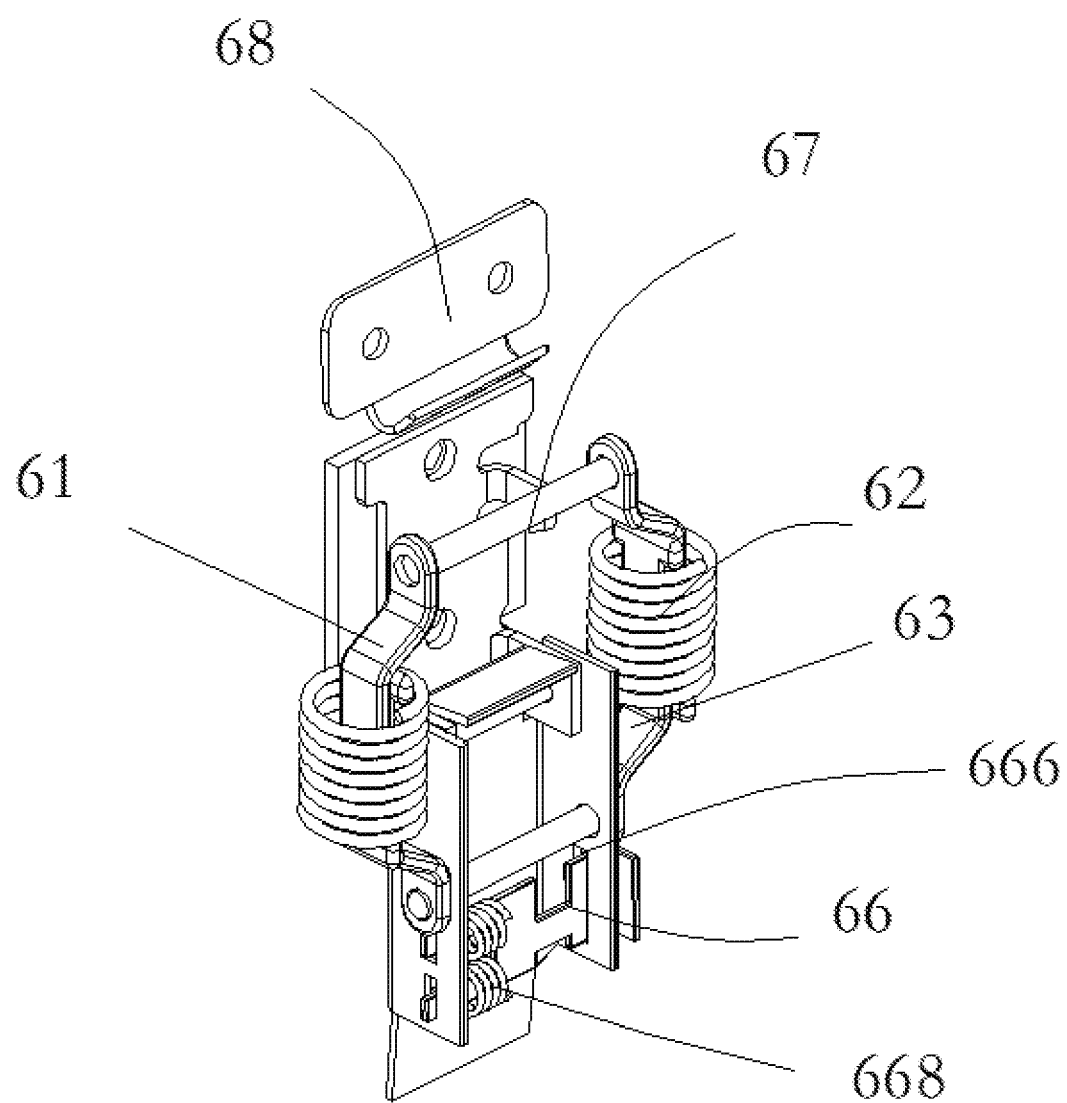
FIG. 38 is a schematic diagram of the structure of the spring lock from the second angle of view.
Figure 39:
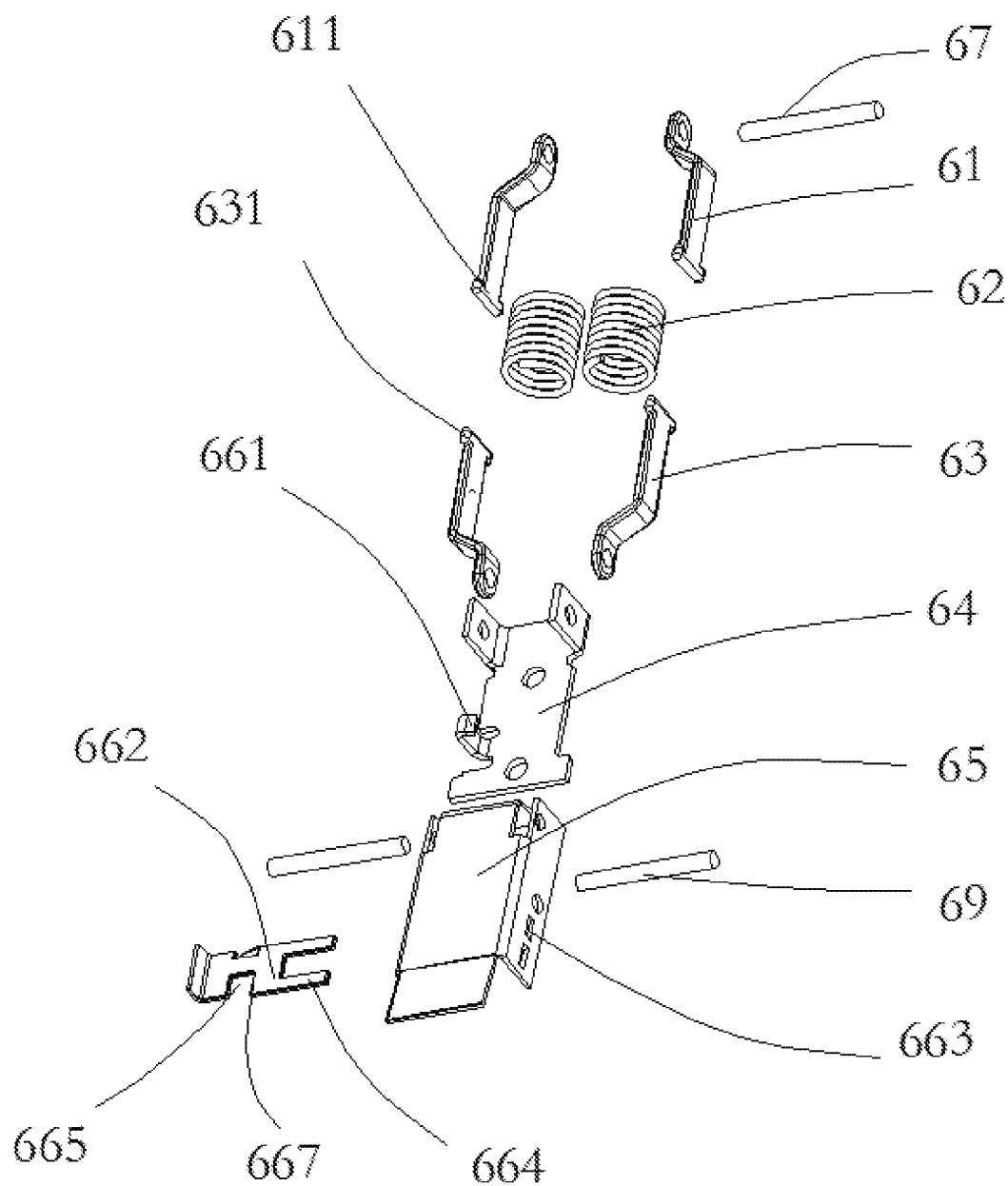
FIG. 39 is an exploded view showing the structures of the spring lock.
Figure 40:
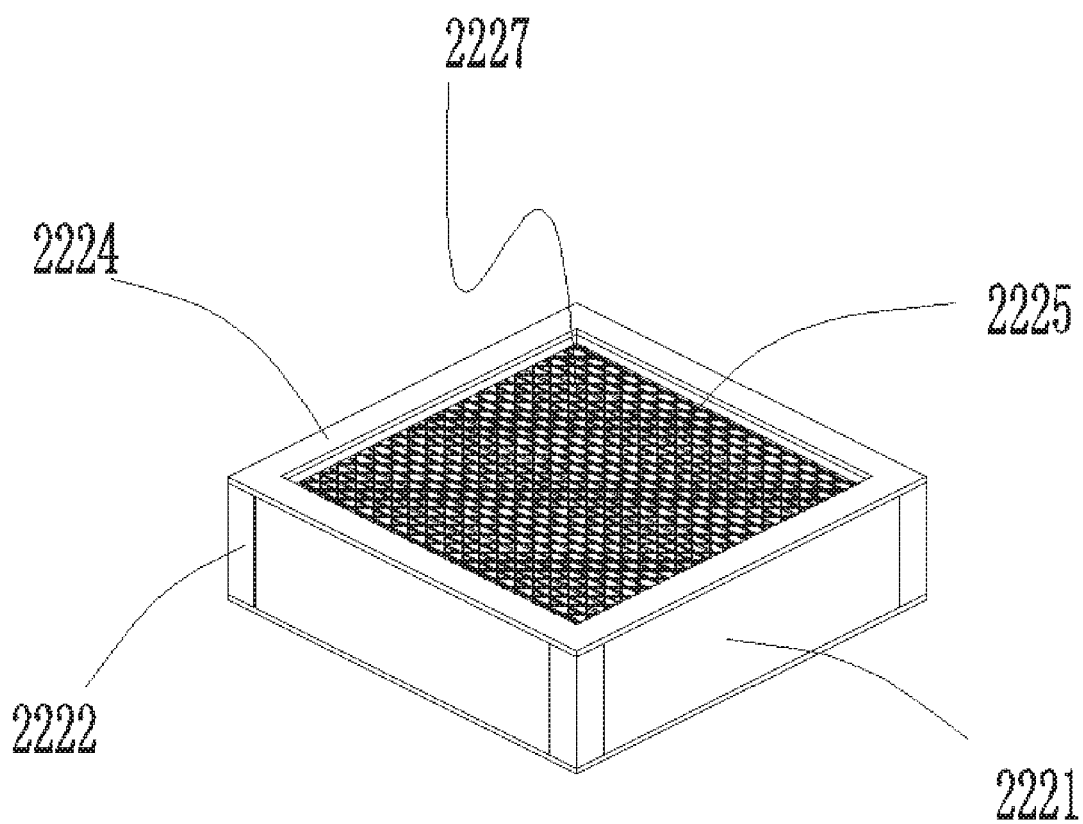
FIG. 40 is a schematic diagram of the structure of the bacteria filtering screen.
Figure 41:
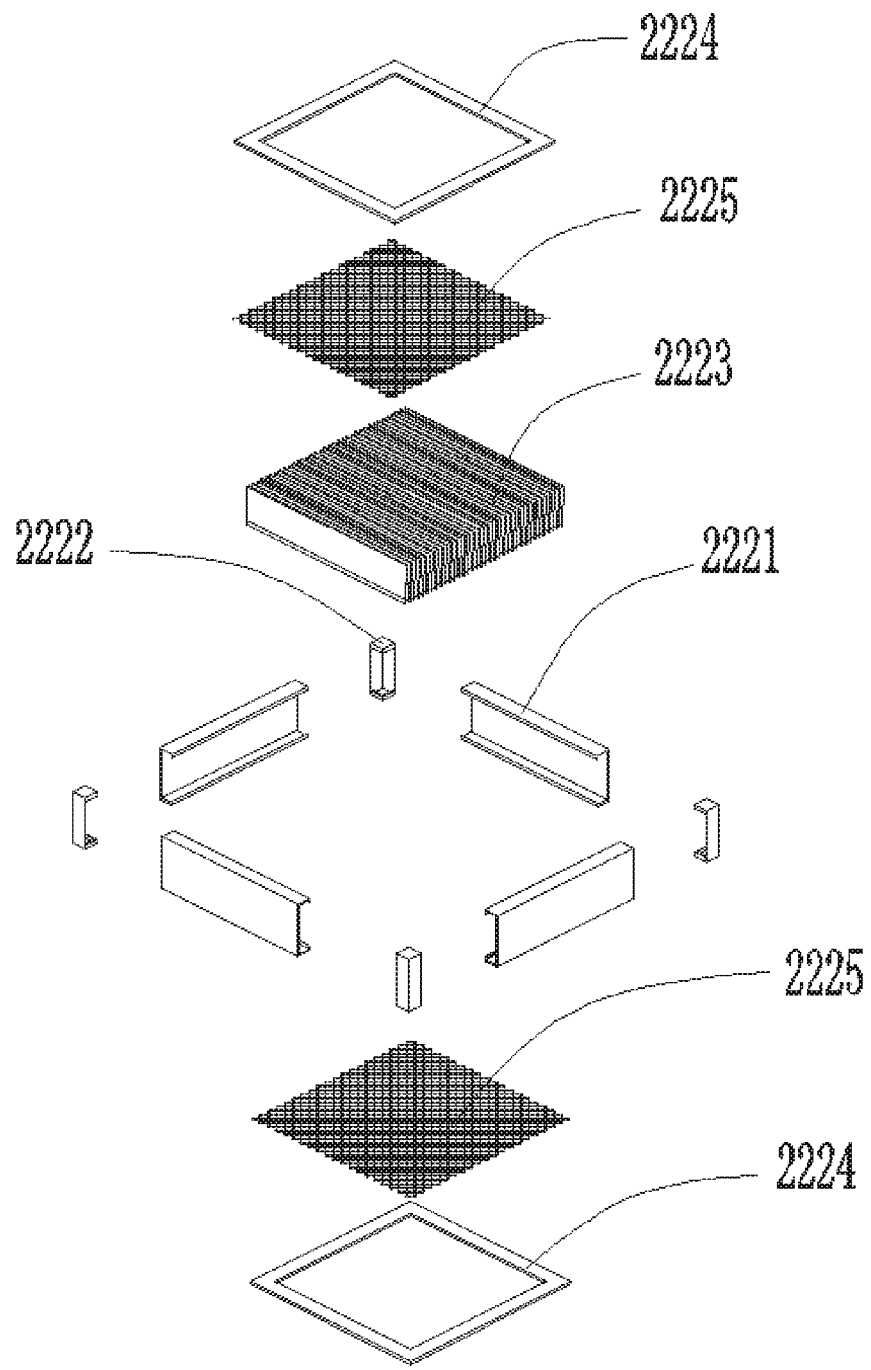
FIG. 41 is an exploded view showing the structures of FIG. 40.
Figure 42:
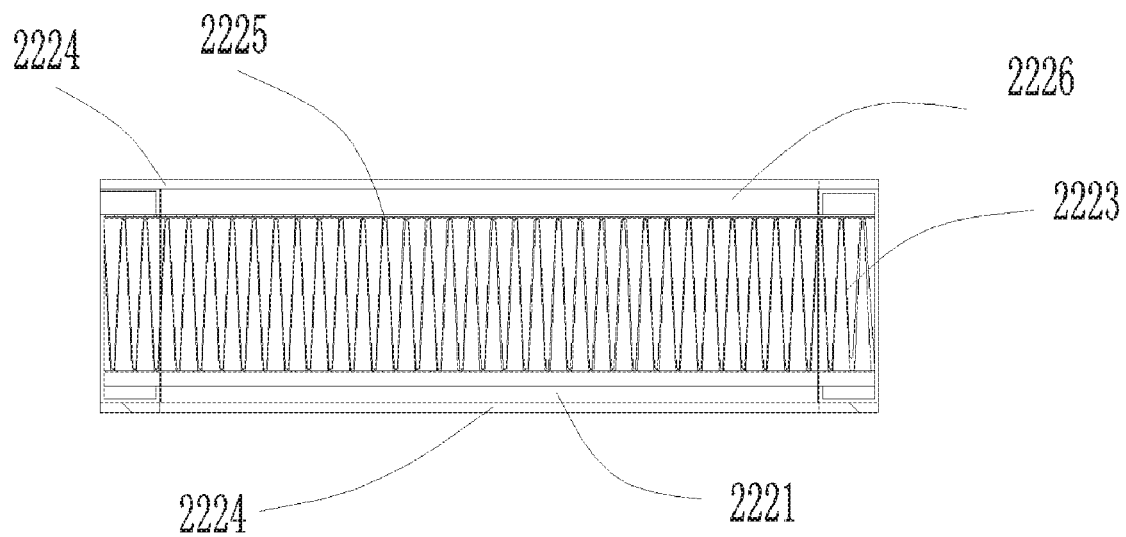
FIG. 42 is a cross-sectional view of FIG. 40.
Figure 43:
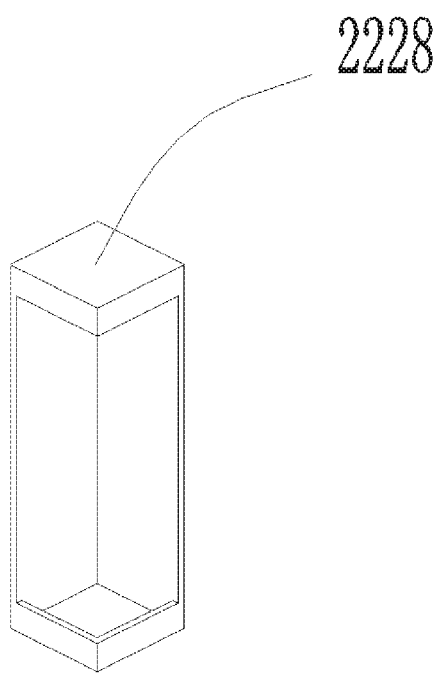
FIG. 43 is a schematic diagram of the structure of the connector.
Figure 44:
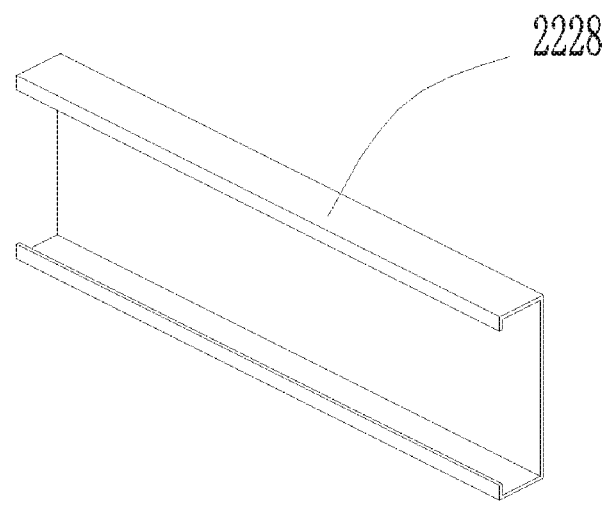
FIG. 44 is a schematic diagram of the structure of the partition profile.
Figure 45:
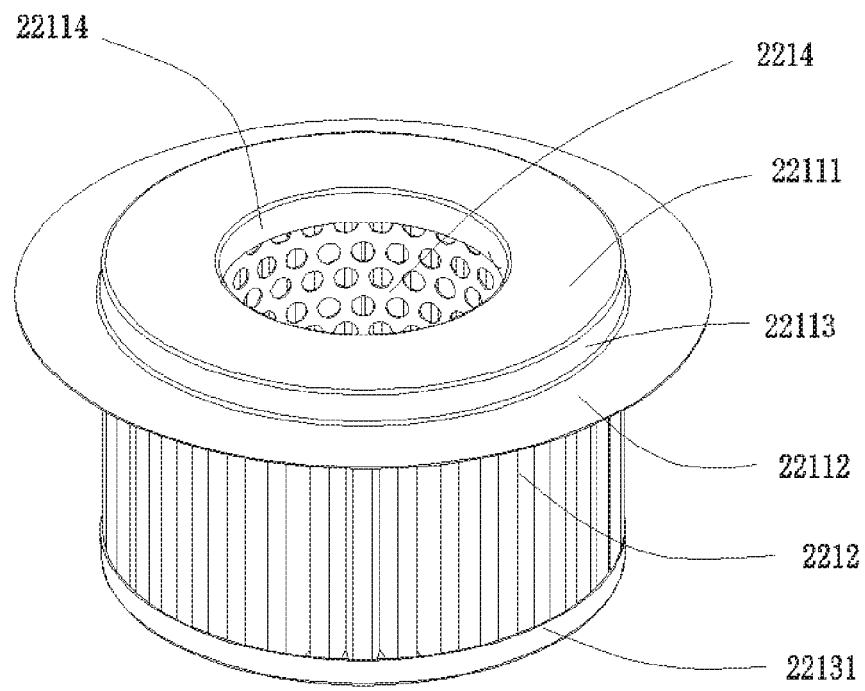
FIG. 45 is a schematic diagram of the structure of the front filtering screen.
Figure 46:
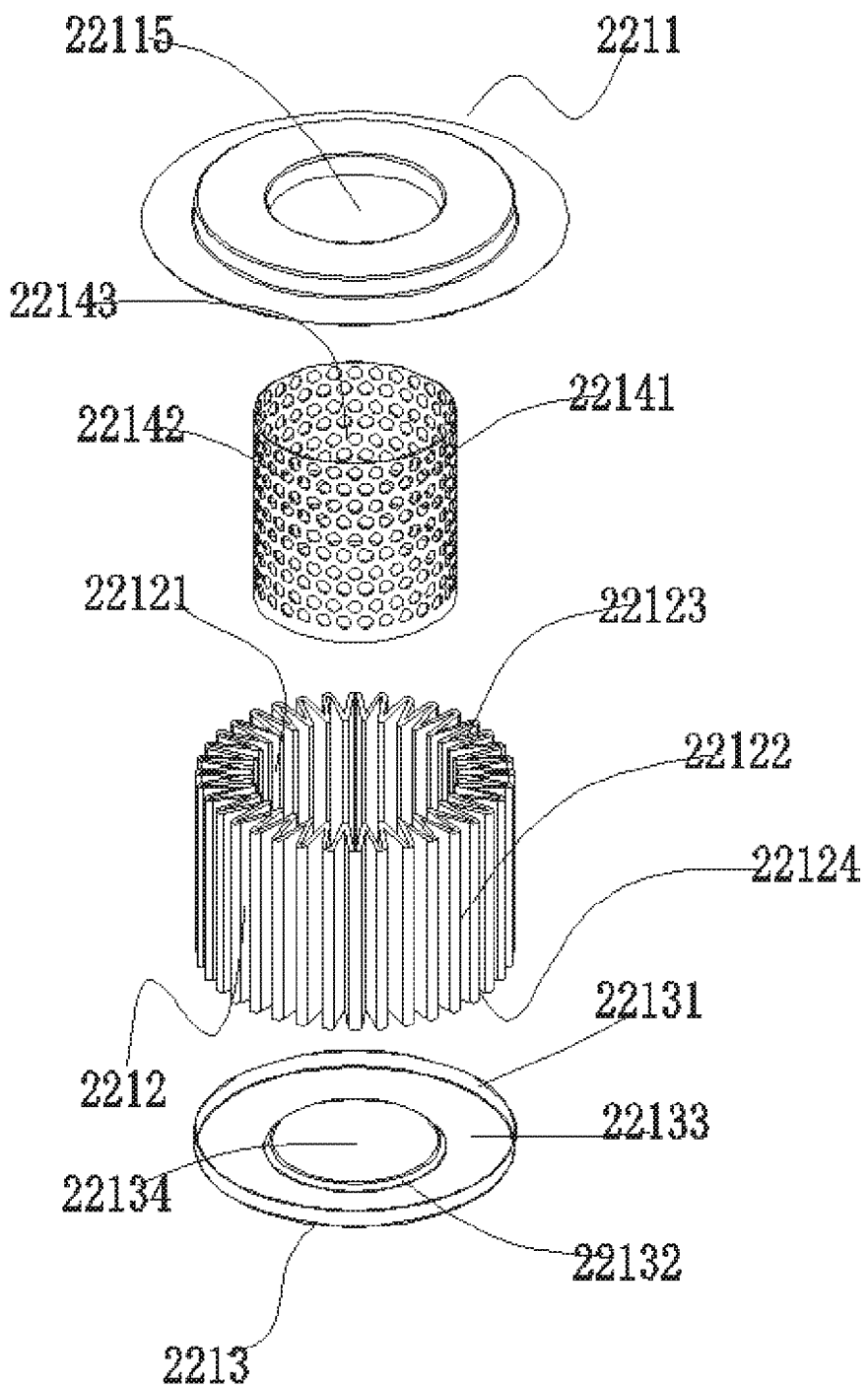
FIG. 46 is an exploded view showing the structures of FIG. 45.
Figure 47:
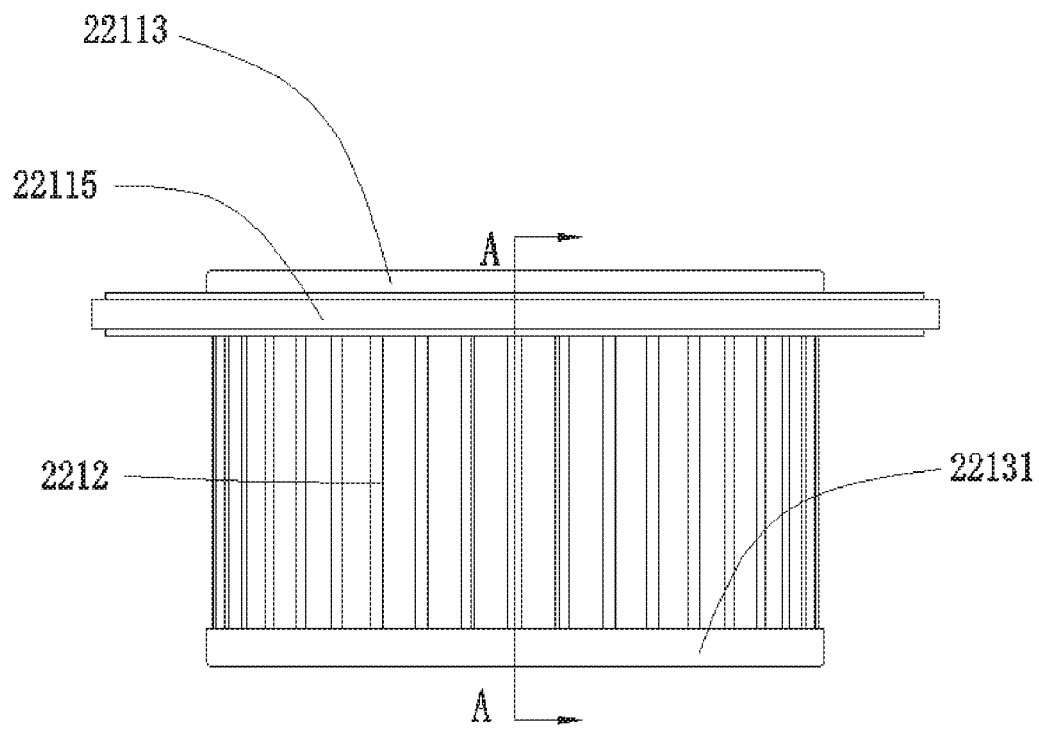
FIG. 47 is the front view of FIG. 45.
Figure 48:
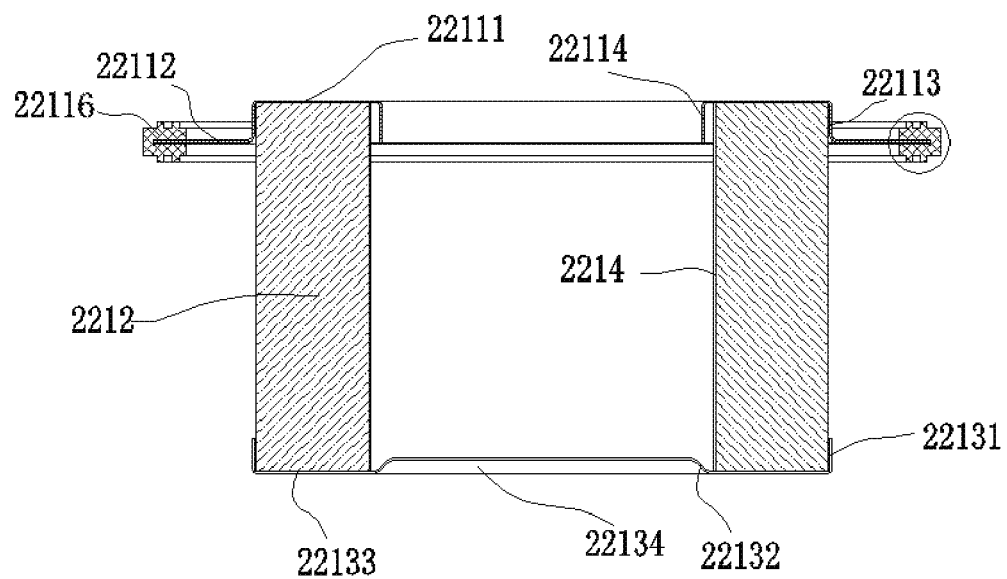
FIG. 48 is a cross-sectional view taken along the section A-A in FIG. 47.
Figure 49:
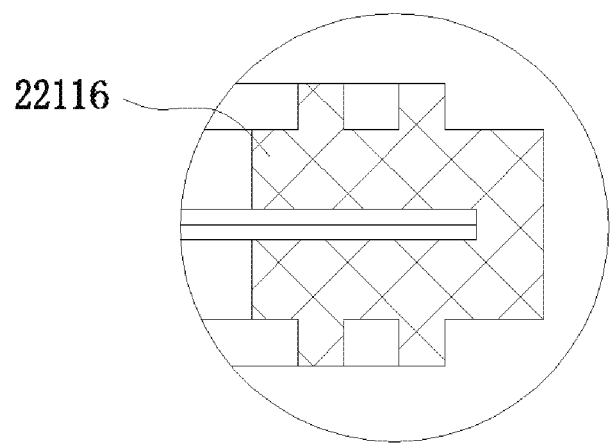
FIG. 49 is a partially enlarged view of the portion encircled in FIG. 48.
Figure 50:
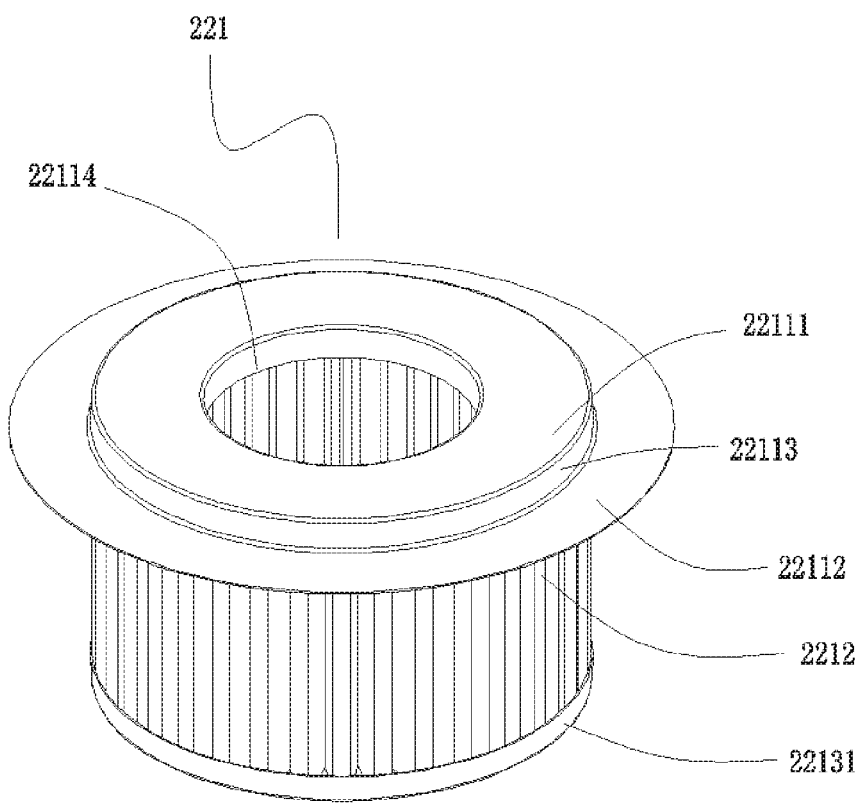
FIG. 50 is a schematic diagram showing the second embodiment of the structure of the front filtering screen.
Figure 51:
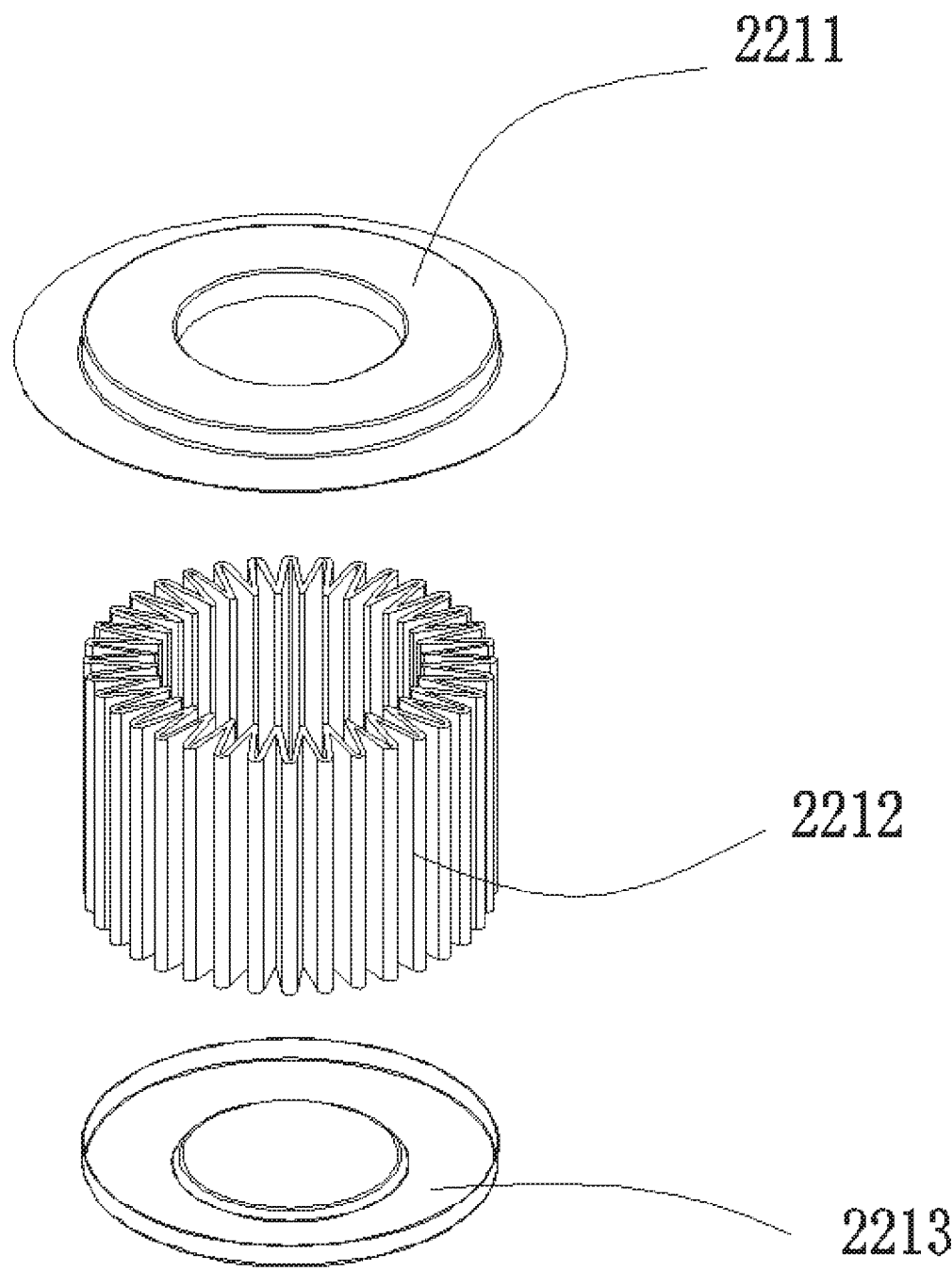
FIG. 51 is an exploded view showing the structures of FIG. 50.

As shown in FIGS. 29-30, unlike the previous embodiment, the photocatalyst 23111 is arranged on the periphery of the ultraviolet sterilization lamp 6. The photocatalyst 23111 has an encircling structure. The ultraviolet light passes through the photocatalyst 23111, and is scattered on the filtering screen to a wider range through the space of the irradiation cavity, which improves the inactivation efficiency of the bacteria.

As shown in FIG. 28, as a preferred embodiment, the receiving surface is arranged on the first side wall 571, and the ultraviolet sterilization lamp 6 is arranged on the receiving surface. The ultraviolet sterilization lamp 6 is arranged on the first side wall 571 (i.e. the side wall where the air intake port 111 is arranged), and the air intake port 111 is arranged directly opposite to the bacteria filtering screen 53.

Figure 20:
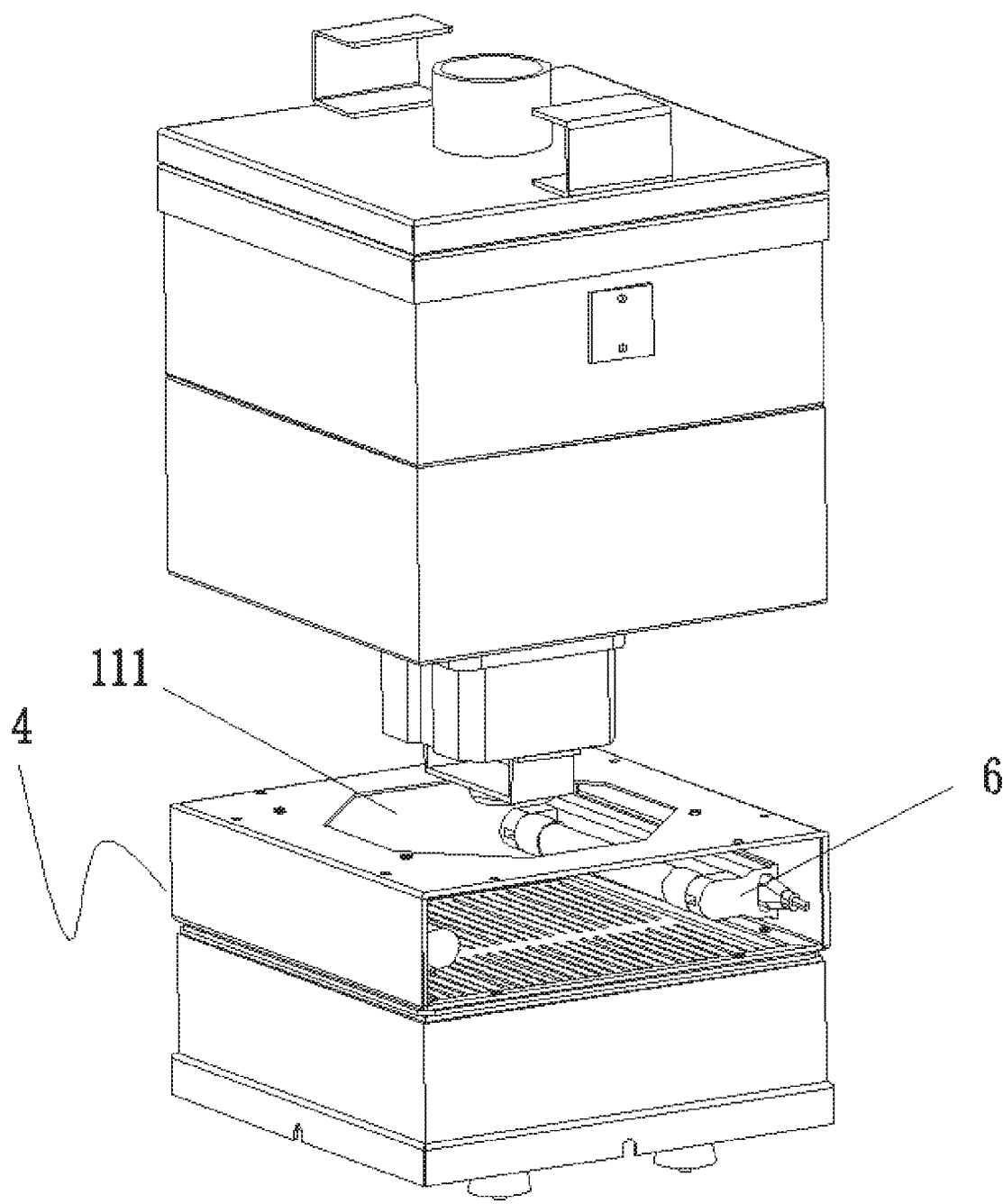
FIG. 20 is a schematic diagram showing the structure of the filtering device arranged on the third side wall.
Figure 21:
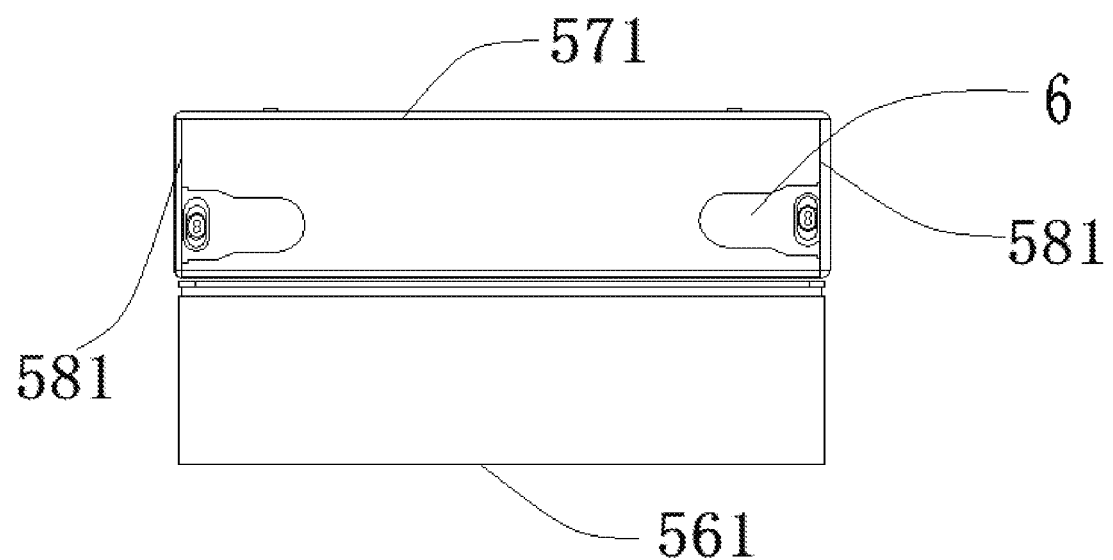
FIG. 21 is a schematic diagram showing the assembly structure of the ultraviolet sterilization lamp in FIG. 20.

As shown in FIGS. 20-21, unlike the previous embodiment, the bacteria filtering mechanism 5 further includes the third side wall 581 connected to the first side wall 571, and the ultraviolet sterilization lamp 6 is arranged on the third side wall 581. The ultraviolet sterilization lamp and the air intake port 111 are not arranged on the same side wall. The first side wall 571 is arranged opposite to the second side wall 561, and the third side wall 581 is connected between the first side wall 571. The ultraviolet sterilization lamp 6 is arranged at the connection between the second side wall 561 and the third side wall 581. A certain distance is reserved between the air intake port 111 arranged on the first side wall 571 and the ultraviolet sterilization lamp 6, so that the ultraviolet light of the ultraviolet sterilization lamp 6 does not irradiate into the air inlet end 121 to avoid aging the air inlet end 121.

Figure 22:
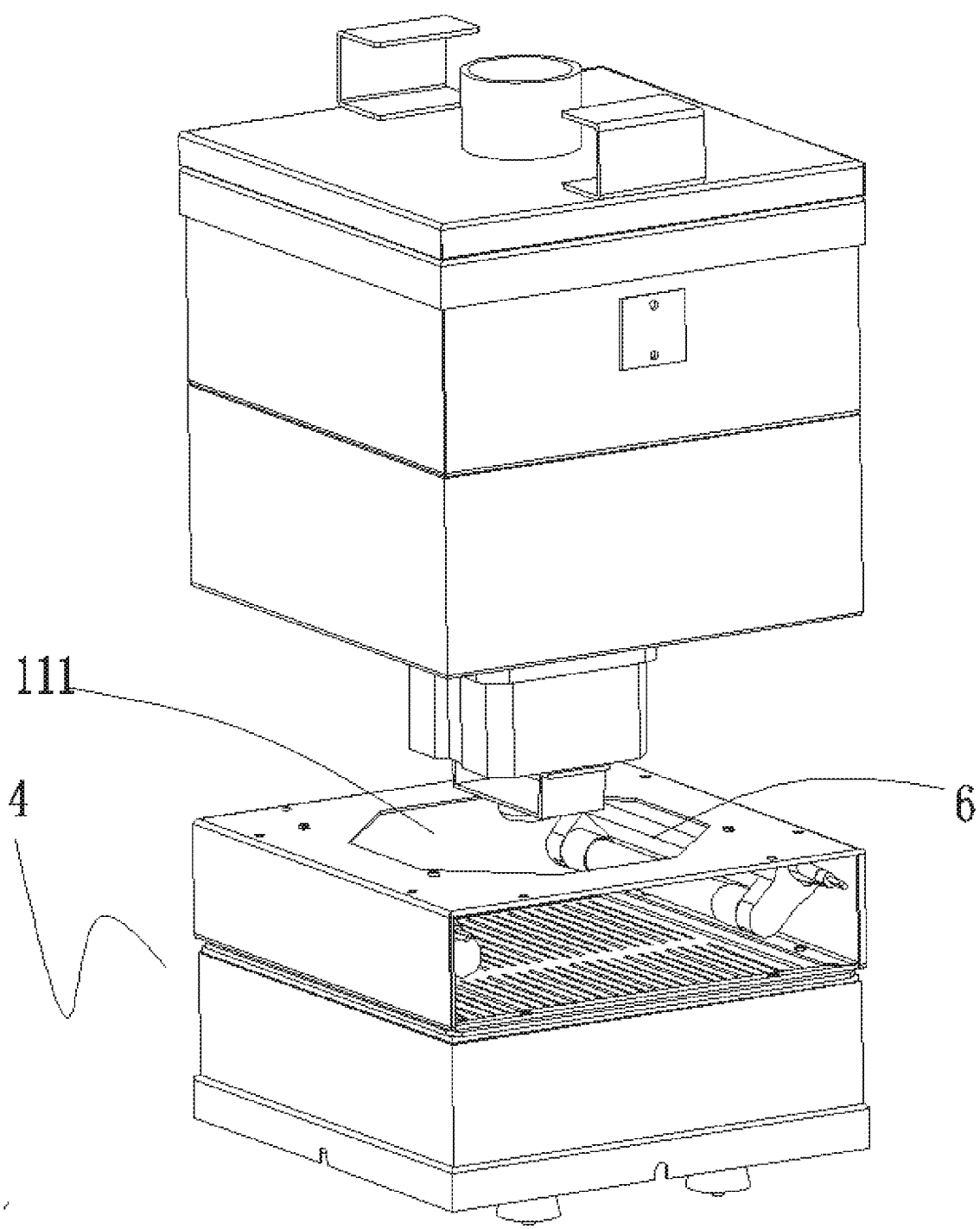
FIG. 22 is a schematic diagram showing the structure of the ultraviolet sterilization lamp arranged between the first side wall and the third side wall.
Figure 23:
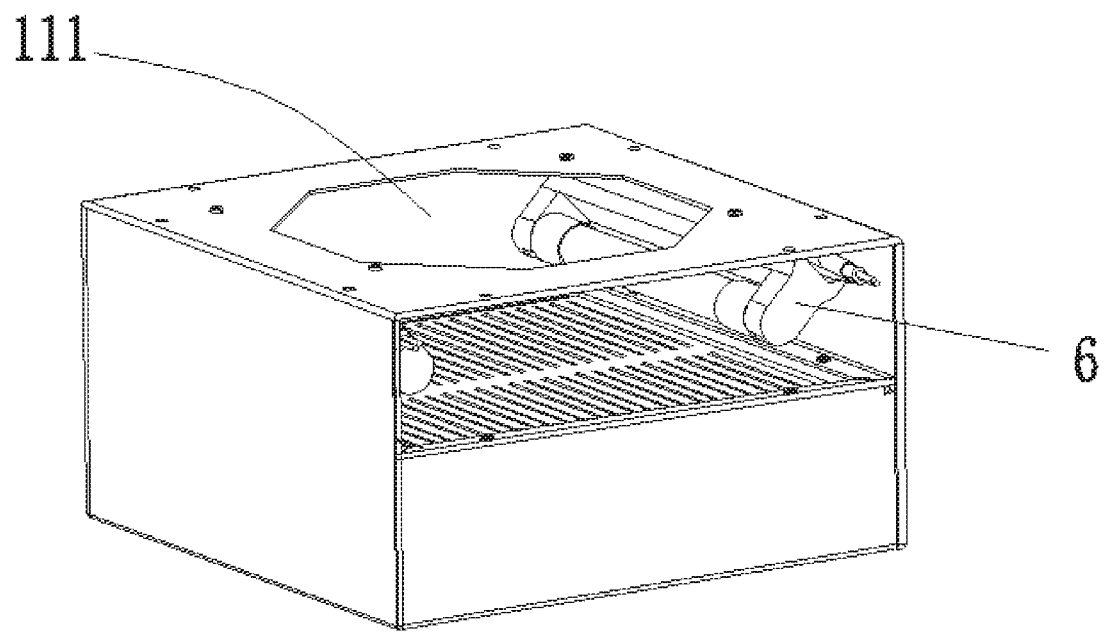
FIG. 23 is a schematic diagram showing the assembly structure of the ultraviolet sterilization lamp in FIG. 22.
Figure 24:
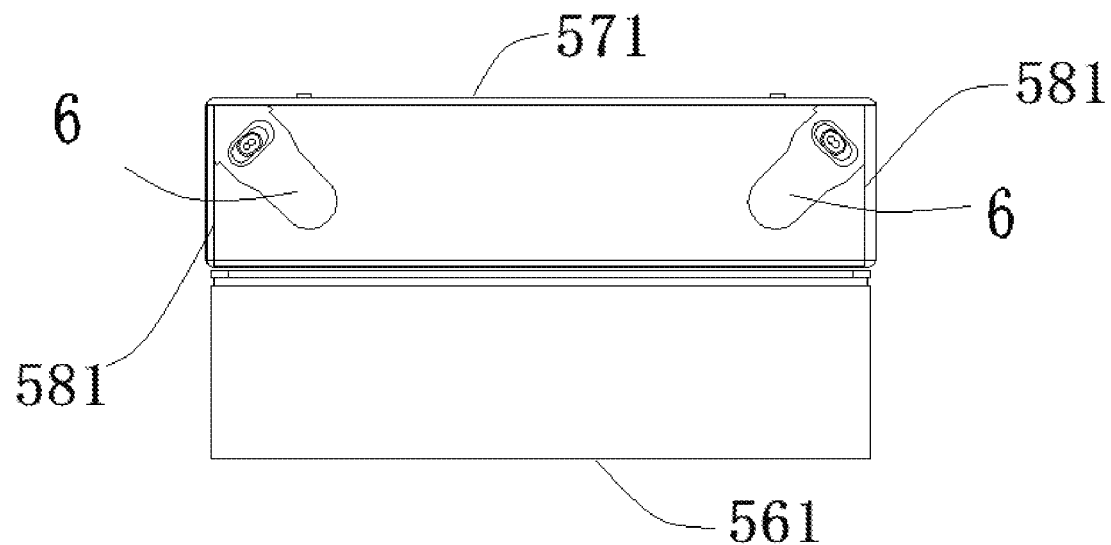
FIG. 24 is a cross-sectional view of FIG. 23.

As shown in FIGS. 22-24, unlike the previous embodiment, the bacteria filtering mechanism 5 further includes the third side wall 581 connected to the first side wall 571, and the ultraviolet sterilization lamp 6 is arranged at the connection between the first side wall and the third side wall 581. The ultraviolet sterilization lamp 6 is arranged at the connection between the first side wall 571 and the third side wall 581, so that the ultraviolet light of the ultraviolet sterilization lamp in the bacteria filtering mechanism 5 can irradiate more adequately to minimize the blind area.

As a preferred embodiment, the ultraviolet sterilization lamp 6 includes a corner connecting plate. The corner connecting plate is connected to the first side wall 571 and the third side wall 581. A certain degree of angle, preferably a right angle, is formed between the first side wall 571 and the third side wall 581. The connecting plate is arranged at the corner between the first side wall 571 and the third side wall 581, and the ultraviolet sterilization lamp 6 is arranged on the connecting plate.

As a preferred embodiment, a plurality of ultraviolet sterilization lamps 6 are arranged. The plurality of ultraviolet sterilization lamps 6 are configured to enhance the irradiation intensity and accelerate the inactivation rate. A plurality of ultraviolet sterilization lamps 6 in the filtering device may be arranged on at least one of the first side wall, the third side wall 581, and the connection between the first side wall and the third side wall 581.

As a preferred embodiment, the suction device includes a plurality of bacteria filtering mechanisms 5. The plurality of bacteria filtering mechanisms 5 work simultaneously to increase the sterilization rate.

Figure 25:
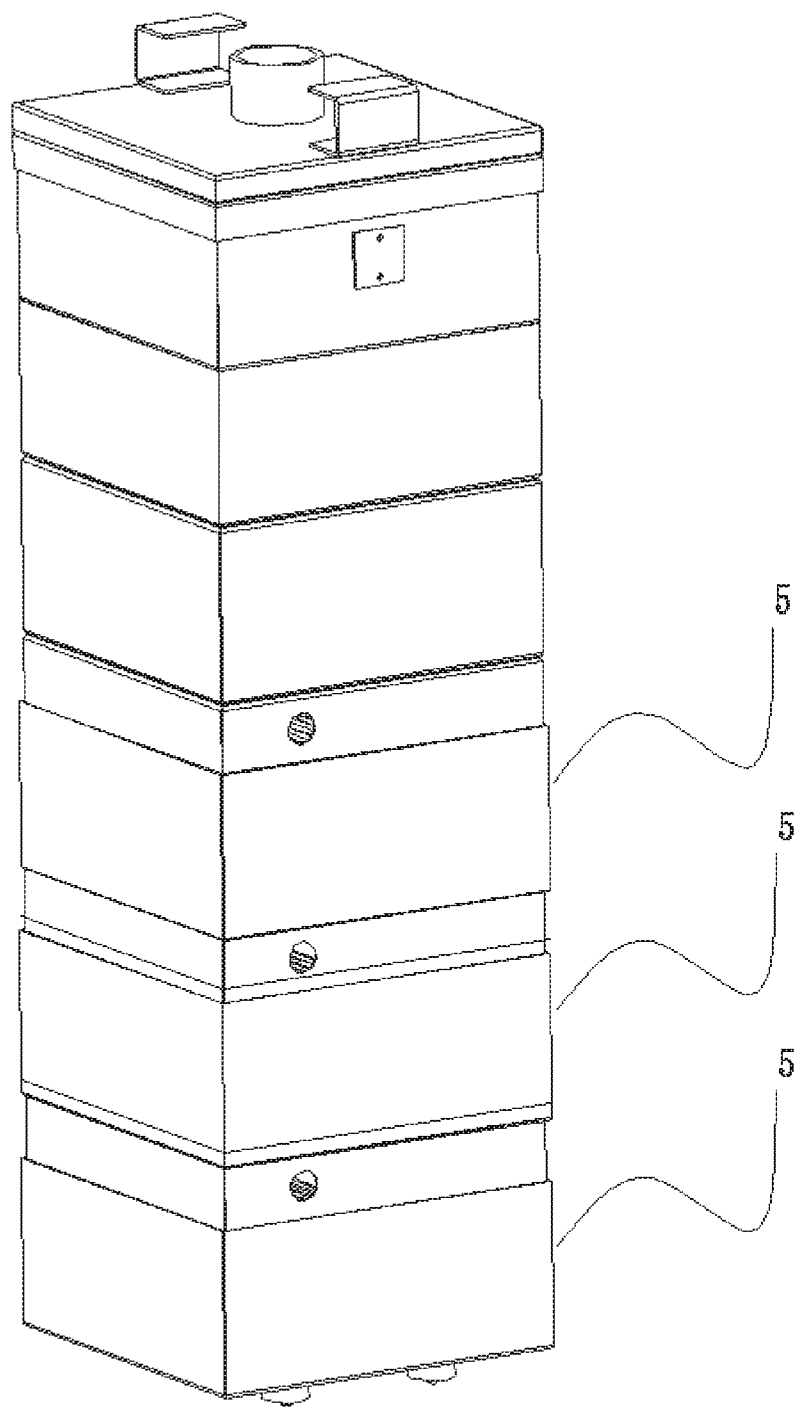
FIG. 25 is a schematic diagram of the structure of the filtering devices connected in series.

As shown in FIG. 25, as a preferred embodiment, a plurality of bacteria filtering mechanisms 5 are connected in parallel. The plurality of bacteria filtering mechanisms 5 are connected by a pipe, or the plurality of bacteria filtering mechanisms 5 are connected to an air intake cavity, so that the air introduced from the front end can smoothly enter into the bacteria filtering mechanism 5. The plurality of bacteria filtering mechanisms 5 connected in parallel can increase the air flow volume for sterilization and increase the sterilization rate.

Figure 26:
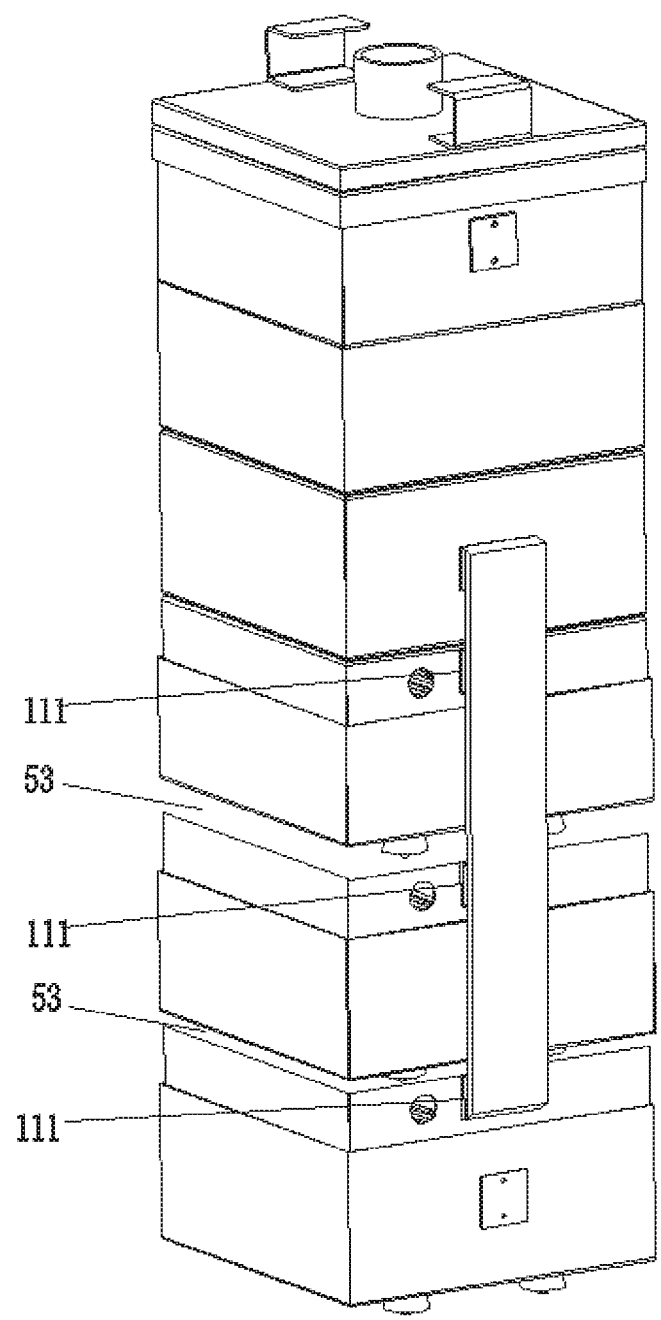
FIG. 26 is a schematic diagram of the structure of the filtering devices connected in parallel.
Figure 27:
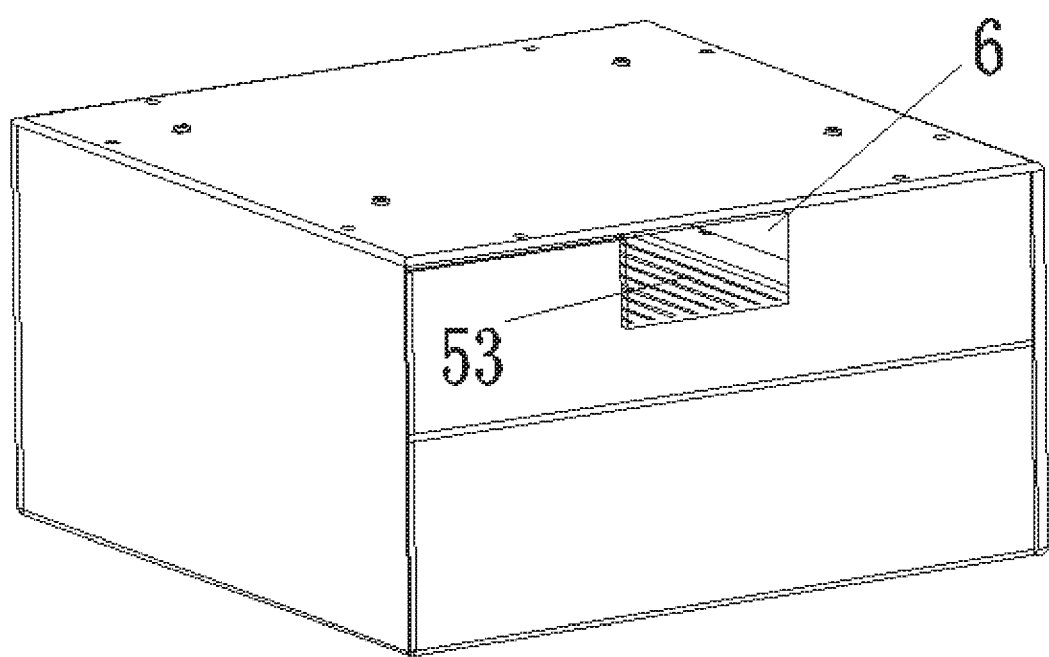
FIG. 27 is a schematic diagram showing the air intake structure of FIG. 26.

As shown in FIG. 26, unlike the previous embodiment, a plurality of bacteria filtering mechanisms 5 are connected in series. The bacteria filtering mechanism 5 includes an air inlet end and an exhaust end. The air inlet end and the exhaust end in two adjacent bacteria filtering mechanisms 5 are connected. The air is filtered many times and the filtered bacteria are inactivated, so that the inactivation effect is improved.

As a preferred embodiment, the bacteria filtering mechanisms 5 can be connected in series-parallel combinations.

As shown in FIGS. 31-51, the respiratory droplet filtering device provided by the present invention includes the air inlet end 121, the exhaust end 58, the fan 8 for providing power, and the treatment unit for filtering and sterilizing the air. The treatment unit includes the front filtering mechanism 4 and the bacteria filtering mechanism 5. The fan 8 is arranged between the front filtering mechanism 4 and the bacteria filtering mechanism 5. The air inlet end 121 is connected to the front filtering mechanism 4, and the exhaust end 58 is connected to the bacteria filtering mechanism 5. The bacteria filtering mechanism 5 further includes the ultraviolet sterilization lamp 6 and the bacteria filtering screen 53. The bacteria filtering mechanism 5 is connected to the front filtering mechanism 4, and the ultraviolet sterilization lamp 6 is arranged corresponding to the bacteria filtering screen 53. The front filtering mechanism 4 and the bacteria filtering mechanism 5 are the functional mechanisms of the treatment unit, wherein, the bacteria filtering mechanism 5 further includes the suction device. The suction device is provided with the ultraviolet sterilization lamp 6 and the bacteria filtering screen 53, and the ultraviolet sterilization lamp is arranged corresponding to the bacteria filtering screen 53. The fan is arranged between the front filtering mechanism 4 and the bacteria filtering mechanism 5. The air inlet end 121 is connected to the front filtering mechanism 4, the exhaust end 58 is connected to the bacteria filtering mechanism 5, and the bacteria filtering mechanism 5 is connected to the front filtering mechanism 4.

In the present invention, the fan 8 is arranged between the front filtering mechanism 4 and the bacteria filtering mechanism 5, and the fan is at the center of the force demand to intake the air at the front end and to discharge the air at the rear end, which can protect the balance between the air introduced into the device and the air discharged out of the device and avoid the backflow of the air in the fan. Moreover, the ultraviolet sterilization lamp 6 is arranged corresponding to the bacteria filtering screen 53, which can quickly inactivate the bacteria filtered on the bacteria filtering screen 53 through the fan.

As a preferred solution, as shown in FIGS. 31-34, the front filtering mechanism 4 includes the front filtering screen 44, the front buckle plate 42 and the front receiving cavity 41. The front filtering screen includes the main panel 441 and the secondary panel 442. There is a smooth transition between the main panel 441 and the secondary panel 442. The front buckle plate 42, the secondary panel 442 and the front receiving cavity 41 are laminated together. The sealing soft material is arranged between the front buckle plate 42 and the secondary panel 442, and the sealing soft material is arranged between the secondary panel 442 and the front receiving cavity 41. The front buckle plate 42, the secondary panel 442 and the front receiving cavity 41 are laminated together to be tightly connected, so that there is a low requirement of the related components for replacing the front filtering screen, and the compactness of the front filtering mechanism 4 can be maintained after the replacement.

As a preferred embodiment, the bacteria filtering mechanism 5 includes the bacteria filtering screen 53, the rear buckle plate 51 and the rear receiving cavity 52. The bacteria filtering screen 53 includes the upper connecting surface 57 and the lower connecting surface 56. The sealing soft material is arranged between the rear buckle plate 51 and the lower connecting surface 56. The sealing soft material 55 is arranged between the upper connecting surface 57 and the rear receiving cavity 52. The rear buckle plate 51, the lower connecting surface 56, the upper connecting surface 57 and the rear receiving cavity 52 are laminated together. The bacteria filtering screen 53 is tightly connected to the device through the sealing soft material 55, so that there is a low requirement of the related components for replacing the front filtering screen, and the compactness of the front filtering mechanism 4 can be maintained after the replacement.

As a preferred embodiment, the front buckle plate 42 and the front receiving cavity 41 are connected by the spring lock 60. The spring lock 60 includes the lock body and the buckle body 68, and the lock body is arranged on the front receiving cavity 41.

As a preferred embodiment, the lock body includes a retractable portion and an anti-release portion. The retractable portion includes the fixed base 64, the flipping member 65 and the hanging buckle 68. The fixed base 64 is fixed on the front receiving cavity 41. The upper end of the flipping member 65 is connected to the fixed base 64, and the middle portion of the flipping member 65 is pivotally connected to the hanging buckle 68.

The invention includes the spring lock 60. The sealing soft material cooperates with the spring lock 60 to double enhance the airtightness of the connection, which can ensure the good airtightness between the front filtering screen and the device and the good airtightness between the bacteria filtering screen 53 and the device. This increases durability under similar strength and prevents the sealing soft material from being damaged by excessive force.

As a preferred embodiment, the hanging buckle 68 includes the retractable spring 62, the upper hanging member 61, the lower hanging member 63, the front connecting shaft 67 and the rear connecting shaft 69. One end of the upper hanging member 61 is the upper anti-release end 611, and the other end of the upper hanging member 61 passes through the upper end of the retractable spring 62 and is connected to the front connecting shaft 67. One end of the lower hanging member 63 is the lower anti-release end 631, and the other end of the lower hanging member 63 passes through the lower end of the retractable spring 62 and is connected to the rear connecting shaft 69. The upper hanging member, the retractable spring and the lower hanging member are combined to form a retractable elastic arm. The lower end of the retractable elastic arm is connected to the middle portion of the flipping member, and the upper end of the retractable elastic arm is connected to the front connecting shaft. The front connecting shaft can be hung and secured in the spring buckle. The flipping member is rotated upward to place the front connecting shaft inside the hanging buckle, and is then rotated downward to press the sealing soft material arranged on the bacteria filtering screen 53 to the secondary panel, so as to ensure that the device is hermetically sealed.

In order to prevent the flipping member from disengagement caused by excessive force, the anti-release portion is further provided. The anti-release portion includes the pin 66, the pin reset spring 668 and the barb 661, wherein the barb 661 is arranged on the fixed base 64. The pin includes the pin reset base 662, the pin notch 665 and the limiting tooth 667. The flipping member is provided with a pin hole and the socket 666 allowing one end of the pin to pass through the pin hole. The socket 666 is configured to fix the pin reset base 662. The pin passes through the pin hole and the pin reset spring 668 and then is inserted into the socket 666. The flipping member has a U-shaped cross section. The pin hole and the socket 666 are oppositely arranged on two sides of the U-shaped flipping member. The barb 661 is arranged in the pin notch 665. When a force is applied on the pin, the barb 661 can be disengaged from the pin notch 665, and the limiting tooth 667 prevents the pin from being disengaged from the pin notch 665 or the socket 666. When an external force is applied on the pin, the pin can move along the direction from the pin notch 665 to the socket 666. When the external force is removed, and the pin is subjected to the force of the pin reset spring to move until the limiting tooth 667 abuts on the side wall of the surface of the flipping mechanism where the pin notch 665 is arranged. The above-mentioned structure has the advantages of simple structure, low cost and fast installation, and can effectively ensure an airtight seal between the front filtering screen, the bacteria filtering screen 53 and the device body.

After the bacteria are filtered through the bacteria filtering mechanism 5, they are filtered and accumulated from the windward surface and are inactivated by the ultraviolet sterilization lamp 6, which prevents bacteria backflow and breeding.

As shown in FIGS. 36 and 40-44, in the present invention, the bacteria filtering screen 53 further includes the windward surface 2227, the frame and the filtering screen 2223. The windward surface 2227 is the front surface of the filtering screen 2223 and is arranged opposite to the air intake port of the sterilization equipment. The air entering the air intake port passes through the windward surface 2227 and is discharged out the other side of the filtering device to filter the bacteria-grade fine particles in the air, and then the bacteria accumulated on the windward surface 2227 are inactivated. The frame covers the outer edge of the filtering screen 2223 along the longitudinal direction and forms a sealing cavity with the external equipment, so that the air entering from the air intake port into the filtering device is unidirectionally filtered through the filtering screen 2223.

One side of the frame on which the windward surface 2227 is arranged is provided with the receiving portion 2228 for ensuring a tight connection with the air intake port. The frame further includes a plurality of partition profiles 2221 and a plurality of connectors 2222. The partition profile 2221 is connected to the connector 2222 in a manner including but not limited to bonding, welding or riveting. The connector 2222 is connected between two partition profiles 2221. In one embodiment, these structures are integrally formed, which is another implementation mode of the technical solution of the present invention.

The plurality of connectors 2222 are end-to-end connected to the plurality of partition profiles 2221 successively at intervals. There is a smooth transition between the surface of the connector 2222 and the surface of the partition profile 2221. The filtering screen 2223 is polygonal. Any partition profile 2221 is connected to the connector 2222. The filtering device provided by the present invention is a highly efficient filtering mechanism. The air can pass through the filtering device, but the fine particles and bacteria cannot pass through. The periphery of the filtering device is surrounded by the partition profiles 2221 and the connectors 2222. The partition profiles 2221 and the connectors 2222 are enclosed to form a hollow box. The filtering screen 2223 is connected to the hollow box, so that the bacteria and particles in the air flowing through the filtering screen 2223 are filtered into the redundant dust cavity, thus achieving the purpose of bacteria filtration.

The length-width-height ratio of the filtering device is 15-25:15-25:3-9. Alternatively, the length-width-height ratio of the filtering device can also be one selected from the group consisting of: 16:16:4, 17:17:3, 17:17:4, 18:17:4, 19:17:4, 20:17:4, 21:17:4, 22:17:4, 17:18:4, 17:19:4, 17:20:4, 17:21:4, 17:22:4, 17:23:4, 17:17:5, 17:18:5, 17:19:5, 17:20:5, 17:21:5, 17:22:5, 17:17:6, 17:18:6, 17:19:6, 17:20:6, 17:21:6, 17:22:6, 17:18:7, 17:19:7, 17:20:7, 17:21:7, 17:22:7, 17:23:7, 17:17:8, 18:18:4, 18:19:4, 18:20:4, 18:21:4, 18:22:4, 18:23:5, 18:18:6, 18:19:6, 18:20:6, 18:21:6, 18:22:6, 18:18:7, 18:19:7, 18:20:7, 18:21:7, 18:22:7, 18:23:7, 18:24:8, 19:19:4, 19:20:4, 19:21:4, 19:22:4, 19:19:5, 19:19:6, 19:19:7, 19:19:8, 20:20:4, 20:17:4, 20:18:4, 20:19:4, 20:20:4, 20:21:4, 20:22:4, 20:20:5, 20:17:5, 20:18:5, 20:19:5, 20:20:5, 20:21:5, 20:22:6, 20:23:7, 20:16:8, 20:17:8, 20:18:8, 20:19:8, 20:20:8, 20:21:8, 20:22:8, 21:21:4, 21:16:4, 21:17:4, 21:18:4, 19:21:4, 21:20:4, 21:21:4, 21:22:

5, 21:21:6, 21:21:7, 21:21:8, 21:21:9, 22:22:4, 22:22:5, 22:22:6, 22:22:7, 22:22:8, 22:22:9, 23:23:4, 23:23:5, 23:23: 6, 23:23:7, 23:23:8, 23:23:9, 24:24:4, 24:24:5, 24:24:6, 24:24:7, 24:24:8, 24:24:9, 25:25:4, 25:25:5, 25:25:6, 25:25: 7, 25:25:8, 25:25:9, 23:22:7, 23:22:8, 23:22:9, 24:22:7, 24:22:8, 24:22:9, 25:22:7, 25:22:8, 25:22:9, 25:22:7. The amount of data of the structure formed by the ratio of 15-25:15-25:3-9 is relatively large, and thus cannot be totally listed. The products formed based on the ratio of 15-25:15-25:3-9 shall fall within the scope of protection of the present invention. The length, width and height of the filtering device are 190-200 mm, 190-200 mm and 45-55 mm, respectively. Specifically, the length of the filtering device is preferably one selected from the group consisting of 191 mm, 192 mm, 193 mm, 194 mm, 195 mm, 196 mm, 197 mm, 198 mm, 199 mm, 200 mm; the width of the filtering device is preferably one selected from the group consisting of 191 mm, 192 mm, 193 mm, 194 mm, 195 mm, 196 mm, 197 mm, 198 mm, 199 mm, 200 mm; and the height of the filtering device is preferably one selected from the group consisting of 45 mm, 46 mm, 47 mm, 48 mm, 49 mm, 50 mm, 51 mm, 52 mm, 53 mm, 54 mm, 55 mm. Preferably, the cross section of the filtering device is square, so that the filtering device can be tightly combined with the external mechanism.

The filtering device further includes the rigid fixed support 2225. The rigid fixed support 2225 is arranged at one side of the windward surface 2227 and is connected to the partition profile 2221. The fixed support 2225 is arranged in a grid shape, and a certain distance is reserved between the fixed support 2225 and the filtering screen 2223 to prevent contamination or distortion of the filtering blade caused by the direct contact with the surface of the filtering screen 2223 during the use of the filtering screen 2223.

The fixed support 2225 is made of a photocatalyst material. The photocatalyst of the fixed support 2225 uses the fixed support 2225 as the substrate material, and the surface of the fixed support 2225 is provided with a photocatalyst coating, which can decompose and inactivate the bacteria. The photocatalyst material mentioned above includes, but is not limited to, nanometer-sized $TiO_2$, ZnO, CdS, $WO_3$, $Fe_2O_3$, PbS, $SnO_2$, ZnS, $SrTiO_3$, and $SiO_2$.

The fixed support 2225 is arranged on both sides of the filtering screen 2223. The fixed support 2225 arranged on the side of the windward surface 2227 will interact with the ultraviolet light. The filter screen 2223 with the photocatalyst coating can be provided with a plurality of fixed supports 2225 above the windward surface 2227 to enhance the photocatalyst effect.

The receiving portion 2228 extends toward the filtering screen 2223 to form a C-shaped cross section of the partition profile 2221. The extended structure arranged in the receiving portion 2228 is in the shape of a table, which facilitates the connection between the filtering device and the air intake port and exhaust port. The filtering device is not integrally formed due to constraints of the production environment of the present invention, such as materials and production conditions, etc. The filtering device can also be integrally formed. Therefore, this technical solution shall fall within the creative spirit of the present invention.

The receiving cotton 2224 is arranged above the receiving portion 2228. The receiving cotton 2224 facilitates the connection between the filtering device and the air intake port and the exhaust port. The receiving cotton 2224 can also be replaced by soft materials such as silica gel, dissimilar materials such as foams or plastics, sealing materials such as adhesive tape, and other materials known by skilled artisans for their desired physical and/or mechanical properties qualifying them for application as herein set forth. It should be noted that the same inventive concept shall fall within the spirit of the protection of the present invention.

The filtering screen 2223 includes a plurality of filtering blades arranged in a wavy shape. Preferably, the filtering blade is formed by folding the filtering screen 2223 to obtain a continuous V-shaped structure with a folded reverse side. The filtering blade is made of glass fibers, which can filter particles of 0.1 nm, 0.2 nm, 0.3 nm, 0.4 nm, 0.5 nm, 0.6 nm, 0.7 nm, 0.8 nm or 0.9 nm in size. A redundant dust cavity is formed between any two filtering blades opposite to each other. The cross section of the redundant dust cavity is V-shaped, and the bacteria can be accumulated upward from the bottom of the V-shaped structure due to the wind force, which increases the filtering area of the filtering screen 2223 and the volume of the redundant dust cavity, and enhances the filtration efficiency.

The filtering screen 2223 further includes a shaping frame. The shaping frame is arranged corresponding to the filtering blade, and the inner surface of the V-shaped opening is adsorbed on the filtering blades.

The drop distance 2226 is formed between the windward surface 2227 and the receiving surface. The windward surface 2227 is provided with the drop distance 2226, so that it is easy to determine the front and reverse sides of the filtering device from the appearance, and the accommodating cavity on the side of the windward surface 2227 is enlarged, which provides favorable conditions for bacterial inactivation.

As shown in FIGS. 45-51, in the present invention, the front filtering screen 221 includes the following mechanisms. The filtering device includes the front filtering screen 221 and the air intake panel 2211. The air intake panel 2211 and the lower end panel 2213 are arranged on the two end surfaces of the front filtering screen 221, respectively. The lower end panel 2213 seals the lower end of the front filtering screen 221 to form a closed cavity. The air entering from the air intake panel 2211 flows unidirectionally, and is filtered by the filtering screen on the inner ring surface 22121 of the front filtering screen 221, so that the dust particles in the air are filtered. The main panel 22111 and the secondary panel 22112 are configured to connect the front filtering screen 221 and the ring surface corresponding to the front filtering screen 221, so that the air entering the filtering device can be discharged only after being filtered by the front filtering screen 221, thus ensuring the quality of the discharged air.

The front filtering screen 221 is in the shape of a cavity, one side of the front filtering screen 221 is provided with the front filtering screen air inlet 22143, and the other side of the front filtering screen 221 is closed. The air intake panel 2211 includes the panel air intake hole 22115, the main panel 22111 and the secondary panel 22112. The panel air intake hole 22115 is arranged in the middle of the main panel 22111, and the secondary panel 22112 is arranged on the periphery of the main panel 22111. The secondary panel 22112 extends outward along the periphery of the main panel 22111 and is in a plane shape. The panel air intake hole 22115, the front filtering screen air inlet 22143 and the front filtering screen 221 are arranged in sequence. The cavity shape mentioned indicates the main body of the front filtering screen 221 for storage, one end of the cavity is open provided with the air inlet, and the other end of the cavity is closed. The front filtering screen 221 can partly filter the air passing therethrough, especially, the particles with a particle size greater than 5 μm.

As a preferred embodiment, a filtering device with the appropriate size is arranged to match the corresponding model of the apparatus, so that the front filtering screen 221 provided by the present invention is compatible with numerous embodiments. The secondary panel 22112 is annular, extends outward along the periphery of the main panel 22111 and is in a plane shape, and has a diameter larger than the diameter of the main panel 22111. The secondary panel 22112 can be connected to the respiratory droplet suction system for filtration. Specifically, the outer diameter of the secondary panel 22112 is less than or equal to 190 mm and can be one selected from the group consisting of 150 mm, 151 mm, 152 mm, 153 mm, 154 mm, 155 mm, 156 mm, 157 mm, 158 mm, 159 mm, 160 mm, 161 mm, 162 mm, 163 mm, 164 mm, 165 mm, 166 mm, 167 mm, 168 mm, 169 mm, 170 mm, 171 mm, 172 mm, 173 mm, 174 mm, 175 mm, 176 mm, 177 mm, 178 mm, 179 mm, 180 mm, 181 mm, 182 mm, 183 mm, 184 mm, 185 mm, 186 mm, 187 mm, 188 mm, 189 mm, and 190 mm. The inner diameter of the secondary panel 22112 is more than 120 mm and can be one selected from the group consisting of 120 mm, 121 mm, 122 mm, 123 mm, 124 mm, 125 mm, 126 mm, 127 mm, 128 mm, 129 mm, 130 mm, 131 mm, 132 mm, 133 mm, 134 mm, 135 mm, 136 mm, 137 mm, 138 mm, 139 mm, 140 mm, 141 mm, 142 mm, 143 mm, 144 mm, 145 mm, and 146 mm. The diameter of the panel air intake hole 22115 ranges from 35 mm to 100 mm, and can be one selected from the group consisting of 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, 51 mm, 52 mm, 53 mm, 54 mm, 55 mm, 56 mm, 57 mm, 58 mm, 59 mm, 60 mm, 61 mm, 62 mm, 63 mm, 64 mm, 65 mm, 66 mm, 67 mm, 68 mm, 69 mm, 70 mm, 71 mm, 72 mm, 73 mm, 74 mm, 75 mm, 76 mm, 77 mm, 78 mm, 79 mm, 80 mm, 81 mm, 82 mm, 83 mm, 84 mm, 85 mm, 86 mm, 87 mm, 88 mm, 89 mm, 90 mm, 91 mm, 92 mm, 93 mm, 94 mm, 95 mm, 96 mm, 97 mm, 98 mm, 99 mm, and 100 mm. The height of the front filtering screen 221 ranges from 45 mm to 120 mm, and can be one selected from the group consisting of 45 mm, 46 mm, 47 mm, 48 mm, 49 mm, 50 mm, 51 mm, 52 mm, 53 mm, 54 mm, 55 mm, 56 mm, 57 mm, 58 mm, 59 mm, 60 mm, 61 mm, 62 mm, 63 mm, 64 mm, 65 mm, 66 mm, 67 mm, 68 mm, 69 mm, 70 mm, 71 mm, 72 mm, 73 mm, 74 mm, 75 mm, 76 mm, 77 mm, 78 mm, 79 mm, 80 mm, 81 mm, 82 mm, 83 mm, 84 mm, 85 mm, 86 mm, 87 mm, 88 mm, 89 mm, 90 mm, 91 mm, 92 mm, 93 mm, 94 mm, 95 mm, 96 mm, 97 mm, 98 mm, 99 mm, 100 mm, 101 mm, 102 mm, 103 mm, 104 mm, 105 mm, 106 mm, 107 mm, 108 mm, 109 mm, 110 mm, 111 mm, 112 mm, 113 mm, 114 mm, 115 mm, 116 mm, 117 mm, 118 mm, 119 mm, and 120 mm.

As a preferred embodiment, the air intake panel 2211 is provided with the flanging corresponding to the inner ring surface 22121, and the lower end panel 2213 is provided with the flanging corresponding to the outer ring surface. The flanging structure can form a groove carrying a certain amount of fluid. By adding the adhesive to the groove, the front filtering screen 221 can be securely bonded to the groove, which adds quality and extends product life.

As a preferred embodiment, the front filtering screen 221 includes the inner ring surface 22121 and the outer ring surface 22122. The panel outer flanging 22113 is arranged between the main panel 22111 and the secondary panel 22112, and the panel outer flanging 13 is arranged along the outer ring surface 22122. The panel inner flanging 22114 is arranged at the panel air intake hole 22115 toward the front filtering screen air inlet 22143, and the panel inner flanging 22114 is arranged along the inner ring surface 22121. Both the panel outer flanging 22113 and the panel inner flanging 22114 are flanged toward the front filtering screen 221. During assembly, the adhesive is injected into the annular groove formed by the panel outer flanging 22113 and the panel inner flanging 22114, and then one end of the front filtering screen 221 is bonded in the annular groove with the adhesive, which has the advantages of high production rate, good sealing effect and high sealing strength, and is significant in production and processing of products.

The upper end surface 22123 of the front filtering screen 221 is bonded to the main panel 22111, and the lower end surface 22124 of the front filtering screen 221 is bonded to the lower end panel 2213.

As a preferred embodiment, the front filtering screen 221 further includes the lower end panel 2213. The lower end panel 2213 is provided with the lower end outer flanging 22131 and the lower end inner flanging 22132. The lower end outer flanging 22131 is arranged at the lower part of the front filtering screen 221 along the outer ring surface 22122 of the front filtering screen 221, and the lower end inner flanging 22132 is arranged at the lower part of the front filtering screen 221 along the inner ring surface 22121 of the front filtering screen 221, thus forming the protrusion 22134 at the middle of the lower end panel 2213 toward the air intake panel 2211. The annular groove 22133 is formed between the lower end outer flanging 22131 and the lower end inner flanging 22132. The lower end outer flanging 22131 and the lower end inner flanging 22132 are flanged so as to extend toward the front filtering screen 221. During assembly, the adhesive is injected into the annular groove formed by the lower end outer flanging 22131 and the lower end inner flanging 22132, and then one end of the front filtering screen 221 is bonded in the annular groove with the adhesive, which has the advantages of high production rate, good sealing effect and high sealing strength, and is significant in production and processing of products.

As a preferred embodiment, the inner side of the inner ring surface 22121 is provided with the muffling wall 22141, and the muffling wall 22141 is annularly arranged along the inner ring surface 22121. The muffling wall 22141 is provided with a plurality of arrayed muffling through holes 22142 through which the air flows into the inner ring surface 22121. The upper end of the muffling wall 22141 is fixedly connected to the panel inner flanging 22114, and the lower end of the muffling wall 22141 is connected to the lower end inner flanging 22132. The muffling wall 22141 is provided with the muffling holes, and the portion between the muffling holes forms the wall body. When the air is blown in, a part of the air is blown on the wall body and another part of the air is blown in the muffling holes. When the speed of the air is excessively high, the muffling holes can effectively reduce the speed of the air, and can also effectively reduce the air noise.

As a preferred embodiment, the panel outer flanging 13 is connected between the main panel 22111 and the secondary panel 22112. The main panel 22111 and the secondary panel 22112 are arranged in two planes parallel to each other, respectively. The main panel 22111 and the secondary panel 22112 are integrally formed with the panel outer flanging 22113, preferably by punching.

The air intake panel 2211 further includes a flexible rubber gasket, and the flexible rubber gasket 22116 is connected to the main panel 22111 and/or the secondary panel 22112. The flexible rubber gasket 22116 is connected to the main panel 22111 and/or the secondary panel 22112.

Although the embodiments of the present invention have been shown and described, for those skilled in the art, it should be understood that various changes, modifications, and replacements can be made to these embodiments without departing from the principle and spirit of the present invention, and the scope of the present invention is defined by the appended claims and equivalents thereof.

What is claimed is:

1. A respiratory droplet suction device, comprising:
A housing containing a filtering device,
wherein the filtering device comprises:
   an air inlet end,
   an exhaust end, and
   a filtering unit arranged between the air inlet end and the exhaust end; the filtering unit is provided with a bacteria filtering screen for filtering and adsorbing bacteria and an ultraviolet sterilization lamp for inactivating the bacteria;
   the filtering unit comprises a first side wall and a second side wall; the first side wall is connected to the air inlet end, and the second sidewall is connected to the exhaust end; and air entering from the air inlet end is filtered by the bacteria filtering screen and discharged out of the exhaust end;
   the ultraviolet sterilization lamp is arranged between the first sidewall and the bacteria filtering screen, and the ultraviolet sterilization lamp is arranged corresponding to the bacteria filtering screen wherein the bacteria filtered and accumulated on the surface of the bacteria filtering screen are continuously irradiated by the ultraviolet sterilization lamp;
   an irradiation cavity is arranged between the first side wall and the bacteria filtering screen; and
   a photocatalyst is arranged in the irradiation cavity, and the photocatalyst is arranged on a periphery of the ultraviolet sterilization lamp and encircles the entire length of the ultraviolet sterilization lamp, wherein the filtering unit is provided with a plurality of the ultraviolet sterilization lamps, wherein the plurality of the ultraviolet sterilization lamps are arranged on at least the first sidewall, a third side wall and a connection between the first side wall and the third side wall;
   wherein the housing comprises:
      a first exhaust mechanism comprising an exhaust port having an air guide sleeve containing a deflector, and the air guide sleeve arranged above the exhaust port and extending upward from the top of the housing, and
      a second exhaust mechanism arranged at a bottom or a sidewall of the housing;
      and wherein an opening connected to the air inlet end is configured to be placed around the mouth of a user.

2. The respiratory droplet suction device of claim 1, wherein
the bacteria filtering screen comprises a windward surface, and
a light of the ultraviolet sterilization lamp is scattered on the windward surface through the irradiation cavity.

3. The respiratory droplet suction device of claim 2, wherein
photocatalyst is arranged above the bacteria filtering screen.

4. The respiratory droplet suction device of claim 1, further comprising a plurality of filtering units connected in parallel.

5. The respiratory droplet suction device of claim 1, further comprising a plurality of filtering units connected in series.

6. A respiratory droplet filtering apparatus, comprising the respiratory droplet suction device of claim 1, an air intake pipe, an exhaust pipe, a fan for providing power, and a treatment unit for filtering and sterilizing an intake air, wherein
the filtering device further comprises a front filtering mechanism; and
the fan is arranged between the front filtering mechanism and the filtering unit, the air intake pipe is connected to an air intake port on the housing, the exhaust pipe is connected to the first exhaust mechanism or the second exhaust mechanism, and the filtering unit is fluidly connected to the front filtering mechanism; the air intake pipe is fluidly connected to the air inlet end of the filtering device, and the exhaust pipe is fluidly connected to the exhaust end of the filtering device.

7. The respiratory droplet filtering apparatus of claim 6, wherein
the front filtering mechanism comprises a front filtering screen, a front buckle plate and a front receiving cavity; the front filtering screen comprises a main panel and a secondary panel, and a smooth transition is provided between the main panel and the secondary panel; the front buckle plate, the secondary panel and the receiving cavity are laminated together.

8. The respiratory droplet filtering apparatus of claim 6, wherein
the filtering device further comprises a rear buckle plate and a rear receiving cavity; the bacteria filtering screen further comprises an upper connecting surface and a lower connecting surface; and
the rear buckle plate, the lower connecting surface, the upper connecting surface and the rear receiving cavity are laminated together.

9. The respiratory droplet filtering apparatus of claim 8, further comprising a spring lock, wherein
the spring lock is configured to lock and press at least one of the front filtering mechanism and the filtering unit, and the spring lock comprises a retractable elastic arm arranged between the front buckle plate and the front receiving cavity.

10. The respiratory droplet filtering apparatus of claim 9, wherein
the spring lock comprises a lock body and a buckle body; the lock body comprises a retractable portion and an anti-release portion; the retractable portion comprises a fixed base, a flipping member and a hanging buckle; the buckle body is fixed on the front buckle plate and/or the rear buckle plate, and the fixed base is fixed on the front receiving cavity and/or the rear receiving cavity; an upper end of the flipping member is connected to the fixed base, and a middle portion of the flipping member is pivotally connected to the hanging buckle.

11. The respiratory droplet filtering apparatus of claim 9, wherein
the retractable elastic arm comprises a retractable spring, an upper hanging member, a lower hanging member, a front connecting shaft and a rear connecting shaft; the retractable spring comprises a retractable body and a spring cavity formed in the retractable body; a first end of the upper hanging member is an upper anti-release end, and a second end of the upper hanging member passes through the spring cavity from an upper end of the retractable spring and is connected to the front connecting shaft; a first end of the lower hanging member is a lower anti-release end, and a second end of the lower hanging member passes through the spring cavity from a lower end of the retractable spring and is connected to the rear connecting shaft.

12. The respiratory droplet filtering apparatus of claim 10, wherein
the anti-release portion comprises a pin, a pin reset spring, and a barb arranged on the fixed base; the pin comprises a pin reset base, a pin notch and a limiting tooth; the flipping member is provided with a pin hole and a socket, wherein one end of the pin passes through the pin hole, and the socket is configured to fix the pin reset base; the pin passes through the pin hole and the pin reset spring and is then inserted into the socket.

13. The respiratory droplet filtering apparatus of claim 12, wherein
the flipping member has a U-shaped cross section, and the flipping member comprises two side walls opposite to each other; the pin hole and the socket are arranged on the two side walls opposite to each other, respectively; the barb is arranged in the pin notch.

14. The respiratory droplet filtering apparatus of claim 10, wherein
the bacteria filtering screen comprises a windward surface, a frame, and a filtering screen;
the frame covers an outer edge of the filtering screen along a longitudinal direction; one side of the frame is provided with the windward surface, a receiving portion for ensuring tight connection, a plurality of partition profiles and a plurality of connectors; the plurality of connectors are end-to-end connected to the plurality of partition profiles successively at intervals, and a smooth transition is provided between a surface of each connector of the plurality of connectors and a surface of each partition profile of the plurality of partition profiles; and
the filtering screen has a polygonal shape.

15. The respiratory droplet filtering apparatus of claim 14, wherein a length-width-height ratio of the respiratory droplet filtering apparatus is 15-25:15-25:3-9.

16. The respiratory droplet filtering apparatus of claim 15, wherein a length of the respiratory droplet filtering apparatus is 190-200 mm, a width of the respiratory droplet filtering apparatus is 190-200 mm, and a height of the respiratory droplet filtering apparatus is 45-55 mm.

17. The respiratory droplet filtering apparatus of claim 14, wherein the bacteria filtering screen further comprises a rigid fixed support, and the rigid fixed support is arranged at one side of the windward surface and is connected to the each partition profile.

18. The respiratory droplet filtering apparatus of claim 17, wherein a surface of the rigid fixed support is provided with a photocatalyst coating.

19. The respiratory droplet filtering apparatus of claim 17, wherein the rigid fixed support is arranged on both sides of the filtering screen.

20. The respiratory droplet filtering apparatus of claim 14, wherein the receiving portion extends toward the filtering screen to form a C-shaped cross section of the each partition profile.

21. The respiratory droplet filtering apparatus of claim 20, wherein a receiving cotton is arranged above the receiving portion.

22. The respiratory droplet filtering apparatus of claim 14, wherein the filtering screen comprises a plurality of filtering blades arranged in a wavy shape, and the plurality of filtering blades are made of glass fibers; a redundant dust cavity is formed between any two filtering blades of the plurality of filtering blades, and the any two filtering blades are opposite to each other.

23. The respiratory droplet filtering apparatus of claim 22, wherein the filtering screen further comprises a shaping frame, and the shaping frame is arranged corresponding to the plurality of filtering blades, and an inner surface of a V-shaped opening is adsorbed on the plurality of filtering blades.

24. The respiratory droplet filtering apparatus of claim 7, wherein the front filtering screen is in a shape of a cavity, a first end of the front filtering screen is provided with a front filtering screen air inlet, and a second end of the front filtering screen is closed; an air intake panel comprises a panel air intake hole, the main panel and the secondary panel; the panel air intake hole is arranged in a middle of the main panel, and the secondary panel is arranged on a periphery of the main panel, the secondary panel extends outward along the periphery of the main panel and is in a plane shape; and
the panel air intake hole, the front filtering screen air inlet and the front filtering screen are arranged in sequence.

25. The respiratory droplet filtering apparatus of claim 24, wherein the secondary panel is annular and has an outer diameter of less than 190 mm and an inner diameter of more than 120 mm; the panel air intake hole has a diameter ranging from 35 mm to 100 mm; the front filtering screen has a height ranging from 45 mm to 120 mm.

26. The respiratory droplet filtering apparatus of claim 24, wherein the front filtering screen comprises an inner ring surface and an outer ring surface;
a panel outer flanging is arranged between the main panel and the secondary panel, and the panel outer flanging is arranged along the outer ring surface, and
a panel inner flanging is arranged at the panel air intake hole toward the front filtering screen air inlet, and the panel inner flanging is arranged along the inner ring surface.

27. The respiratory droplet filtering apparatus of claim 26, wherein the front filtering screen further comprises a lower end panel, and the lower end panel is provided with a lower end outer flanging and a lower end inner flanging; the lower end outer flanging is arranged at a lower part of the front filtering screen along the outer ring surface of the front filtering screen, and the lower end inner flanging is arranged at the lower part of the front filtering screen along the inner ring surface of the front filtering screen.

28. The respiratory droplet filtering apparatus of claim 27, wherein an inner side of the inner ring surface is provided with a muffling wall, and the muffling wall is provided with a plurality of arrayed muffling through holes, wherein the air flows through the plurality of arrayed muffling through holes into the inner ring surface; and
an upper end of the muffling wall is fixedly connected to the panel inner flanging, and a lower end of the muffling wall is connected to the lower end inner flanging.

29. A respiratory droplet electric suction system, comprising the respiratory droplet filtering apparatus of claim 6, a suction arm and a main body, wherein
the main body comprises the housing, an air intake port, the fan, the filtering mechanism, a muffling mechanism and the first exhaust mechanism and the second exhaust mechanism;
the suction arm comprises a first end and a second end, the second end is connected to the air intake port, and the first end is provided with the opening connected to the air inlet end and that is configured to be placed around a mouth of a user for air admission; the air is pumped by the fan to successively pass through the opening, the first end, the second end and the air intake port into the main body;

the fan, the filtering mechanism and the muffling mechanism are all arranged in the housing; the air flows through the filtering mechanism and the fan, and is discharged through the first exhaust mechanism or the second exhaust mechanism.

30. The respiratory droplet electric suction system of claim 29, wherein the air guide sleeve guides the air to flow from the top of the housing to a side wall of the housing to discharge the air downward, and a filter cotton is arranged in the air guide sleeve.

31. The respiratory droplet electric suction system of claim 29, wherein the suction arm comprises a fixed arm, a long arm, a short arm and a positioning arm; wherein, the fixed arm is arranged vertically and a first end of the fixed arm is fixed on an upper portion of the housing; a first end of the long arm is pivotally connected to a second end of the fixed arm; a first end of the short arm is pivotally connected to a second end of the long arm, and a rear end of positioning arm is pivotally connected to a second end of the short arm; the opening is arranged at a front end of the positioning arm, and the opening has a incrementally decreasing size toward the front end of the positioning arm; a filter cotton is arranged in the short arm.

32. The respiratory droplet electric suction system of claim 30, wherein a sound insulation cotton with a concave portion and a convex portion is arranged on an outer wall of an inner liner and an inner wall of a shell.

* * * * *